(12) United States Patent
Hew et al.

(10) Patent No.: US 6,307,020 B1
(45) Date of Patent: Oct. 23, 2001

(54) INTRACELLULAR ANTIFREEZE POLYPEPTIDES AND NUCLEIC ACIDS

(75) Inventors: Choy Hew, Thornhill; Zhiyuan Gong, Toronto, both of (CA)

(73) Assignee: HSC Research and Development Ltd. Partnership, Toronto (CA)

( * ) Notice: Subject to any disclaimer, the term of this patent is extended or adjusted under 35 U.S.C. 154(b) by 0 days.

(21) Appl. No.: 09/117,121

(22) PCT Filed: Jan. 30, 1997

(86) PCT No.: PCT/CA97/00062
§ 371 Date: Nov. 20, 1998
§ 102(e) Date: Nov. 20, 1998

(87) PCT Pub. No.: WO97/28260
PCT Pub. Date: Aug. 7, 1997

Related U.S. Application Data
(60) Provisional application No. 60/010,920, filed on Jan. 31, 1996.

(51) Int. Cl.$^7$ .................................................. C07K 1/00
(52) U.S. Cl. ........................... 530/350; 530/350; 530/300; 435/69.1; 435/68.1; 435/69.7; 435/91.1; 435/320.1; 435/419; 435/252.3; 536/23.5
(58) Field of Search .................................. 435/419, 69.1, 435/68.1, 69.7, 91.1, 320.1, 252.3; 530/350, 300; 426/656, 321; 514/773

(56) References Cited

U.S. PATENT DOCUMENTS
5,118,792   6/1992   Warren et al. ........................ 530/350

FOREIGN PATENT DOCUMENTS
| WO -A-90/ | | | |
|---|---|---|---|
| 13571 | 11/1990 | (WO) .............................. | C07K/7/10 |
| WO 92/16618 | 10/1992 | (WO) ............................ | C12N/15/00 |

OTHER PUBLICATIONS

Alignments.*
Greenfield, et al., "Computed Circular Dichroism Spectra for the Evaluation of Protein Conformation," *Biochemistry* 8:4108–4116 (1969).
Ananthanarayan, et al., "Structural Studies on the Freezing-–Point–Depressing Protein of the Winter Flounder *Pseudopleuronectes Americanus* ," *Biochem. Biophys. Res. Comm.* 74:685 (1977).
DeVries, "Antifreeze peptides and glycopeptides in cold-–water fishes," *Annu. Rev. Physiol.* 45:245–260 (1983).
Pickett, et al., "Sequence of an antifreeze protein precursor," *Eur. J. Biochem.* 143:35–38 (1984).
Scott, et al., "Antifreeze protein genes are tandemly linked and clustered in the genome of the winter flounder," *Proc. Natl. Acad. Sci. USA* 82:2613–2617 (1985).

Kao, et al., "The relationship between molecular weight and antifreeze polypeptide activity in marine fish," *Can. J. Zool.* 64:578–582 (1986).
Scott, et al., "Structural variations in the alanine–rich antifreeze proteins of the pleuronectinae," *Eur. J. Biochem.* 168:629–633 (1987).
Ananthanarayan, et al., "Antifreeze Proteins: Structural diversity and mechanism of action," *Life Chemistry Reports* 7:1–32 (1989).
Chakrabartty, et al., "Structure–Function Relationship in a Winter Flounder Antifreeze Polypeptide," *J. Biol. Chem.* 264:11313–11316 (1989).
Davies, et al., "Biochemistry of fish antifreeze proteins," *FASEB J.* 4:2460–2468 (1990).
Lee, J., et al., "The reduction of the freezing point of tobacco plants transformed with the gene encoding for the antifreeze protein from winter flounder," *Symposium On Molecular Strategies For Crop Improvement Held At The 19$^{th}$ Annual UCLA (University of California—Los Angeles) Symposia On Molecular And Cellular Biology, J. Cell. Biochem. Suppl.* 14 Part E, p. 303 (Abstract) (Apr. 16–22, 1990).
Davies, et al., "Antifreeze protein pseudogenes," *Gene* 112(2):171–178 (1992).
Gong, et al., "Tissue distribution of fish antifreeze protein mRNAs," *Can. J. Zool.* 70:810–814 (1992).
Valero, et al., "Fish Skin: An effective barrier to ice crystal propagation," *J. Exp. Biol.* 164:135–151 (1992).
Wen, et al., "A model for binding of an antifreeze polypeptide to ice," *Biophys. J.* 63:1659–1662 (1992).
Gong, et al., "Zinc and DNA Binding Properties of a Novel LIM Homeodomain Protein Isl–2," *Biochem.* 33:15149–15158 (1994).
Gong, et al., "Transgenic Fish in Aquaculture and Development Biology," *Current Topics in Developmental Biology* 30:178–214 (1995).
Griffith, et al., "Antifreeze proteins and their potential use in frozen foods," *Bioteca Adv.* 13(3):375–402 (1995).
Sicheri, et al., "Ice–binding structure and mechanism of an antifreeze protein from winter flounder," *Nature* 375:427–431 (1995).

(List continued on next page.)

*Primary Examiner*—Karen Cochrane Carlson
*Assistant Examiner*—Hope A. Robinson
(74) *Attorney, Agent, or Firm*—Townsend and Townsend and Crew LLP

(57) ABSTRACT

A family of related intracellular skin type antifreeze polypeptides and corresponding coding nucleic acids are provided. These are the first skin type intracellular antifreeze polypeptides and coding nucleic acids ever reported. The polypeptides are naturally expressed in the skin of Winter Flounder, and skin specific promoters are also provided. The polypeptides are used to make cells cold-resistant, and to improve the palatability of cold foods and liquids. Cold resistant eukaryotes and prokaryotes, including plants, animals and bacteria are made using the skin-type intracellular antifreeze polypeptides and nucleic acids.

14 Claims, 20 Drawing Sheets

OTHER PUBLICATIONS

Gong, et al. "The antifreeze protein genes of the winter flounder, *Pleuronectus americanus*, are differentially regulated in liver and non–liver tissues," *Biochem. Biophyl. Res. Commun.* 206(1):387–392 (1995).

Gong, et al., "Skin antifreeze protein genes of the winter flounder, *Pleuronectes americanus*, encode distinct and active polypeptides without the secretory signal and prosequences," *J. Biol. Chem.* 271(8):4106–4112 (Feb. 23, 1996).

* cited by examiner

```
HPLC-6  DTASDAAAAAALTAANAKAAAELTAANAAAAAATAR
sAFP1   MDAPARAAAATAAAAKAAAEATKAAAAKAAAATKAAAH
```

Figure 2

```
         1               10              20              30          40
         MDAPARAAAATAAAAAKAAAEATKAAAAKAAAATKAAAAKAAAATKAAAH
Clone #
sAFP1  (S4)            ----K----------------A---------------G-AR
sAFP2  (P12, S3)       ----K----------------A----------D----K-AR
sAFP3  (P9)            ----K----------------A---------------G-AH
sAFP4  (P7, P8)        ----K----------------A---------------G-AR
sAFP5  (L3, S2, S11)   ----A----------------A-------*-------G-AR
sAFP6  (L4)            ----A----------------A---------------AR
sAFP7  (S9, S10)       ----A----------------A----AE---AKAAAATKAAAAAAAR
sAFP8  (P13, S6)       ----K----------------A---------------G-AR
F2                     ----K----------------A---------------AR
11-3
```

Figure 4

```
F2   ttacaaaacaagttcatactggcctggatggtcgccacacttcctgttgatgtgaacca   60

F2   gtcggagccgacgccctgctgcgtcacaaatcaaagtgaataaatagaggctgctccct  120

F2   aaaagtttCATCAGGACTTCAAACACTTTCACTGTCGACCACTCAGAATCACTGACAT   180
S3                                                         ------
            M  D  A  P  A  K  A  A  A  A  T  A  A  K  A  A  A  E
F2   CAACATGGACGCCACCAGCCAAAGCCGCCGCCGCCACCGCCGCCAAGGCCGCCGC       240
S3   -------------------------

A  T  A  A  A  A  A  K  A  A  A  A  A  T  K  A  G  A  A  R
F2   AGAAGCCACCGCCGCCGCCAGCTGCCAAAGCAGCAGCCGCCACCAAAGCCGGAGCAGCCCG 300
S3                      *

F2   TTAATGATCGTGGTCGTCTTGATGTGGGATCATGTGAACATCTGAGCAGCAGAGATGTTAC 360
S3

F2   CAATCTGCTGAATAAACCCTGAGAAGCTGATTGTTA                          395
S3   -------------------T----G-(poly A)
```

Figure 5 ttacaaaacaagttcatactggcctggatggtcgccacacttcctgttgatgtgaacca 60
gtcggagccgacgccctgctgcgtcacaaatcaaagtgaataatagaggctgctccct 120
aaaagtttCATCAGGACTCAAACACTTTTCACTGTCGACCACTCAGtacgtgaacact 180
cactttgttctcttacaaattgttttactgtaaatatcttgggaaggaaggaaggata 240
tctgcattatccgagggccattgttttacagcagcggtgaaagatgaagatcttcat 300
ccgtgtcgtgatggtgaaagtttgttctgaacctcattggaagaaacagattcatgt 360
        oct-1
gttcaggcttaaacctgcaaaaatctgagctctgttaaatcatgggaaacaacttataa 420
ttcagtcagggctggaaaactcttttatatgcacagaagaagaagagatgtgatcttta 480
gttcatcaccatgaaacatcatcagcagttaaagtctgtctgcttcagtatcaccggcc 540
agttccagtgcctgtttgaccctgtttaacacaagatggccacctggaccatctttattt 600
acataatgtttacatcagcactcctgtattcagccctaaacttaaagaggcctcactt 660
cctgatctggtgacctgctggttgaaggaaacagagtttgagaggcagcagaaca 720
aatgatttagtttgaatgaagaagctgtcatttgattttatgtttggagggggggggg 780

Figure 6A

```
ggggatcaccaccacacagatattgaacactgtcatcactgagttcggtgaaagtgaaga   840
accagtacatgttgtgatatataatcataataattatataatataccattaatctc       900
tgcagAATCACTGACATCAACATGGACGCCACCAGCCAAGCCGCCAGCCACCGCCCGCC    960
GCCGCCAAGGCCGCCGCCAGAAGCCCGCCCAGTGCCAAAGCAGCAGCCGCCACC        1020
AAAGCCGGAGCAGCCCGTTAATGATCGTGGTCGTCTTGATGTGGGATCATGTGAACATCT  1080
GAGCAGCGAGATGTTACCAATCTGCTGAATAAACCTGAGAAGCTGATTGTTAAAAACCAA  1140
GTGTCCTGTTCATTTCATCTCTGAAAGTCCGTCACAGTTTCTGTAGATCATGTAGACTCC  1200
AGGAAGTGATGCCATTGTGCTGTGTTGAACCTGCAGGG                        1236
```

Figure 6B

```
1    ACCACATCTT CATTTGTAG  TGAACCAGTG CTCCCTACAA GTTCTCAAAA TGGCTCTCTC   60
61   ACTTTTCACT GTCGGACAAT TGATTTTCTT ATTTTGGACA ATGAGAATCA CTGAAGCCAG  120
121  CCCCGACCCC GCAGCCAAAG CCGCCCCAGC AGCAGCTGCC GCCCCTGCCG CAGCCGCCCC  180
181  AGACACCGCC TCTGACGCCG CCGCTGCAGC CGCCCTTACC GCCGCCAATG CCGCCGCCGC  240
241  CGCCAAACTC ACCGCCGACA ACGCCGCCGC CGCCGCAGCA GCCACCGCCA GAGGTTAAGG  301
301  ATCGTGGTCG TCTTGATGTG GG                                           322
```

Figure 7

```
ttacaaaacaagttcatactggatggttgccacaccttcctgttgatgtgaaccagtcgg      60
agccgacgccctgctgcgtcacgaaatcaaaagtgaataatagaggctgctccctaaaag    120
ttttCATCAGGACTCAAACACTTTTCACTGTCGACCACTCAGtacgtgaacactcactt    180
tgtttctcatacaaatctggttttactgtaaatatcttgggaaggaaggaaggatatctg    240
cattatcctgagggccatttgttttacagccagcggtgaaagatgaagatcttcatcca    300
tgttcgtctgatgaaagtttgttctgaaccttcagtggaagaaacagattcatgtctt     360
              oct-1
caggcttaaacctgcaaaaatctgagctctgtgttaaatcatgggaacaactttttaattc   420
agtcaggctgaaaactattttatatgcacagaagaagaagtgatctttagttcat         480
caccatgaaacatcatcagcagttaaagtctgtctgcttcagtatcaccggccagttcc     540
agtgctcatgttcctgatcagcttggtttgaatgatataaaacgattgagtgcctgtt     600
tgaccctgtttaacacagattggacgcatggaccatctttattacataatgttttaca     660
tcagcacttcctgttttcagccctaaacttaaagaggcctcatggaaacttcctgatgat   720
ctggtgacacctgctggttgaaggaaacagagtttgagaggcagcagaaaaatgatttt   780
```

Figure 8A

```
agtttgaatgaagaagctgtgtcatttattttatatttggagggggggggggatcac    840
cacacacagatattgaacactgtcatcactgggttcggtgaagtgaagaaccagtacat  900
gttgtgatatatattatcataataattataataccattaatctctgcagAATC        960
ACTGACATCAACATGGACGCACCAGCCAAAGCCGCCACCGCCGCCCGCCCAAG        1020
GCCGCCGCAGAAGCCACCGCCGCCCAAAGCAGCAGCCGCCACCAAAGCCGCA         1080
GCAGCCCGTTAATGATCGTGGTCGTCTTGATGTGGGATCATGTGAACATCTGAGCAGCGA 1140
GATGTTACCAATCTGCTGAATAAACCTGAGAAGCTGTTTGTTTAAAACCAAGTGTCCTGT 1200
TCATTTCATCTCTGAAACTCATTCACAGTTTCTGTAGATCATGTTTTTATTTTGTTCAGA 1260
CGATGTTGAACTGGATCAGAATCCAGA                                  1287
```

Figure 8B sAFP1 (S4)

```
  1       AC TGT CGA CCA CTC AGA ATC ACT GAC ATC AAC ATG GAC GCA CCA GCC  47
 48  AGA GCC GCA GCC ACC GCC AAG GCC GCC AAG GCC ACC AAG GCC GCA GAA GCC  95
 96  ACC AAA GCC GCA GCC AAA GCA GCT GGG ATC ATG TGA ACA TCT GCA GCC 143
144  CAT TAA TGA TGA TCG TGG TCT TGA TGT GGG ATC ATG TGA ACA TCT GAG 191
192  CAG CGA GAT GTT ACC AAT CTG AAA CCT GAG AAG CTG TTT GTT 239
240  GA                                                     241
``` sAFP2 (S3)

```
  1       TTT CAC TGT CGA CCA CTC AGA ATC ACT GAC ATC AAC ATG GAC GCA CCA  48
 49  GCC AAA GCC ACC GCC AAG GCC GCT GCC AAG GCC GCC AAG GCC GCA GAA  96
 97  GCC ACC GCC GCC GCA GCA GCA AAA GCA GCA GCC AAA GCC GGA 144
145  GCA GCC CGT TAA TGA TCG TGG TCT TGA TCG ATC GGG ATC ATG TGA ACA 192
193  TCT GAG CAG CGA CGA GAT GTT ACC AAT CTG AAT AAA CCT GAG AAG CTG 240
241  TTT GTT GA                                                       248
``` sAFP3 (P9)

```
  1       GT CGA ACA CTC AGA ATC ACT GAC ATC AAC ATG GAC GCA CCA GCC AAA  47
 48  GCC GCC GCA GCC ACC GCC AAG GCC GCC AAG GCC GCC AAA GCC GCC ACC  95
 96  GCC GCC GCC AAA GCA GCA GAC ATC ATG TGA ACA TCT GAG CAG CCA GCC 143
144  CGT TAA GGA TCG TGG TCT TGA TGT GGG ATC ATG TGA ACA TCT GAG 191
192  CAG CGA GAT GTT ACC AAT CTG AAT AAA CCT GAG AAG CTG TTT TTT 239
240  A                                                              240
```

Figure 10A sAFP4 (P7)

```
  1       GT CGA CCA CTC AGA ATC ACT GAC ATC AAC ATG GAC GCA CCA GCC AAA  47
 48  GCC GCC GCA GCC ACC GCC GCC AAG GCC GCC GCA GAA GCC ACC  95
 96  GCC GCC GCA GCT GCC AAA GCA GCA GCC AAA ATG ATG ACA TCT GAG191
144  CAT TAA TGA TCG TGG TCT TGA TGG ATC ATG CCT GAG AAG CTG TTT GTT239
192  CAG CGA GAT GTT ACC AAT CTG CTG                                  262
240  GAA AAA AAA AAA AA
``` sAFP5 (S2)

```
  1          CT TTT CAC TGT CGA CCA CTC AGA ATC ACT GAC ATC AAC ATG GAC GCA  47
 48  CCA GCC AAA ACC GCC GCC GCA ACC GCC GCC GCT GCC AAA GCC ACC  95
 96  GAA GCC ACC GCA GCA GCA GCA GCT GGG ATC ATG TGA ACA143
144  GCA GCC CAT GTT TGA TGA TGA CCT AAT AAA CCT GAG AAG ACA191
192  TCT GAG CAG CAG CGA GAT GTT ACC AAT CTG CTG                  CTG239
240  TTT GTT GA                                                     247
```

Figure 10B

```
sAFP6 (L4)
  1               C AGA ATC ACT GAC ATC AAC ATG GAC GCA CCA GCC AAA GCC GCC GCA  46
 47  GCC ACC GCC AAA GCA GCC AAG GCC GCC AAA GCC GCA GAA GCC GCC GCA  94
 95  GCT GCC TGA TCT TGA TGT AAT GGA GCA TCT GAG ACC GCC CGT TGA TCG 142
143  TGG TCG TCT TGA TGT GGG ATC ATG GAG AAG CAG CGA GAT GTT 190
191  ACC AAT CTG AAT AAA CCT GTT GA                                228 sAFP7 (S9)
  1  CAC TGT CGA CCA CTC AGA ATC ACT GAC ATC AAC ATG GAC GCA CCA GCC  48
 49  GCC GCC GCA GCC ACA GCC GCC AAG GCC GCC AAG GCC GCC GAA GCC  96
 97  ACC GCA GCT TAA GCC AAA GCA GCA TGC TCT TGC TGT GGG ATC ATG GCA 144
145  GCC CGT GGA TCG TGG TCG TGC TCT TGC TGT GGG ATC ATG GAG AAG TCT 192
193  GAG CAG CGA GTT ACC AAT GTT CTG AAT AAA CCT GAG AAG CTG TTT 240
241  GTT TA                                                        245 sAFP8 (S6)
  1  TT CAC TGT CGA ACA CTC AGA ATC ACT GAC ATC AAC ATG GAC GCA CCA  47
 48  GCC GCC GCC ACC GCA GCT GCC ACC GCC AAG GCC GCC GAA GCC  95
 96  GCC ACC GCC GCA AAA GCC GCA GCC GCA GCC ACT GCC GAA GCC 143
144  GCC GCC GCA GCA GCA TCA TGC TCT TGC TGT GGG ATC ATG GCC GCC 191
192  GCC CGT TAA GGA TCG TGG TCA TGC TCT TGC TGT GGG ATC ATG GAG TCT 239
240  GAG CAG CGA GAT GTC ACC AAT GTT TTG AAT AAA GCT GAG AAG CTG TTT 287
288  GTT TA                                                        292
```

INTRACELLULAR ANTIFREEZE POLYPEPTIDES AND NUCLEIC ACIDS

CROSS REFERENCE TO RELATED APPLICATIONS

This application claims priority to U.S. Ser. No. 60/010,920, filed Jan. 31, 1996.

BACKGROUND OF THE INVENTION

The survival of cellular organisms is dependent on the physical properties of water. The freezing point of liquid water sets the lower limit for the survival of most cells, because the formation of ice causes dehydration and osmotic damage to the cell. Organisms which inhabit sub-zero environments have special adaptations which permit the organism to survive. For example, Arctic and Antarctic fish which live in cold seawater have various macromolecular antifreeze polypeptides in the serum of their blood. Such antifreeze polypeptides are a mixture of glycoproteins having a range in relative molecular mass ($M_r$) from about 2,500 to 34,000 (antifreeze glycoproteins, or "AFGPs") and antifreeze polypeptides (AFPs) with $M_r$ from about 3,300 to 12,000. Ananthanarayanan (1989) *Life Chemistry Reports* 7:1–32 provides an overview of AFPs and AFGPs. See also DeVries (1983) *Annu. Rev. Physiol.* 45: 245–260; Davies et al. (1990) *FASEB J.* 4: 2460–2468 and Warren et al U.S. Pat. No. 5,118,792.

At present, three distinct types of AFPs have been characterized from a variety of cold water fish. See, Davies et al. (1990) FASEB J. 4: 2460–2468; and Griffith and Ewart et al. (1995) *Bioteca Adv.* 13(3): 375–402, and references therein. Type I AFPs are alanine-rich, ((α-helical polypeptides, found in many right eye flounders and sculpins. Type II AFPs are enriched with half cystine and are found in sea raven, smelt and herring. Type III AFPs are globular proteins found in several Zoarcoid families including eelpout and wolfish. The AFGPs, which are found in three families of Antarctic fish and polar cods, largely consist of a tripeptide repeat (Ala-Ala-Thr) with a disaccharide attached to the threonyl residue.

Although the different AFPs and AFGPs are structurally distinct, they share the ability to inhibit ice crystal growth by binding to the ice surface. At present, the AFGPs and AFPs have been isolated from serum, and their DNA sequences deduced by cDNA cloning from the liver. All of the proteins described to date are synthesized as larger precursor polypeptides containing the signal peptides, indicating a secretory role for the polypeptides.

AFPs in the liver (liver type AFPs) from the winter flounder, *Pleuronectus americanus*, has been studied extensively in terms of its protein structure and function, gene organization, gene expression and regulation. The genome of the winter flounder contains multiple copies of liver or serum type AFP genes, most of which are arranged as regular tandem repeats (Scott et al. (1985) *Proc. Natl. Acad. Sci. USA*. 82: 2613–2617).

SUMMARY OF THE INVENTION

A new class of AFPs is discovered and described herein. The new class of AFPs, termed "skin-type" AFPs have several features which are different from all previously described AFPs, including the fact that the AFPs are not secreted, i.e., the skin-type AFPs are intracellular. Genomic Southern analysis shows that like the liver-type AFP genes, there are multiple copies of the skin type AFPs (30–40 copies in winter flounder). While the previously described liver-type AFP genes are specifically expressed in the liver, and, to a less extent, in intestine, the skin-type AFP genes are expressed in all tissues examined (including the liver) and abundantly in exterior tissues, i.e. skin, scales, fin and gills, showing that skin type AFPs have a protective role in these exterior tissues.

In one preferred class of embodiments, the invention provides isolated skin-type intracellular antifreeze polypeptides (AFPs). In this embodiment, the AFPs have an N terminal MDAP subsequence (SEQ ID NO:1), and an internal AATAAAAKAAA subsequence (SEQ ID NO: 2). More preferably, the N terminal sequence is an MDAPA sequence (SEQ ID NO:9). The AFPs do not have a signal sequence (i.e., the polypeptides do not have a pre sequence). The AFPs have the physical ability to induce a concentration-dependent decrease in the freezing point of an aqueous solution such as $H_2O$.

In some preferred embodiments, skin type AFPs comprise the sequence MDAPAX$_1$AAAATAAAAKAAAEATX$_2$AAAAX$_2$AAAX$_3$T (SEQ ID NO:3); wherein X$_1$ is selected from the group consisting of R, K, and A; X$_2$ is selected from the group consisting of K and A; and X$_3$ is selected from the group consisting of A, D and a bond.

Particularly preferred polypeptides have a $M_r$ of about 3400, but the $M_r$ can vary substantially, for instance due to multiple skin-type antifreeze polypeptide domains being connected into a single polypeptide, or due to the addition of non-functional amino acids, e.g., at the carboxyl terminus of the protein. Typically the $M_r$ of skin-type AFPs will be about 2500 to about 13,000, more typically about 3,000 to about 6,000, yet more typically about 3200 to about 4,000. Typically, the skin-type AFPs are between about 30 and about 100 amino acids in length, more typically between about 35 and 55 amino acids in length, and usually about 35–45 amino acids in length. However, specific examples are provided herein which exceed the usual 35–45 amino acids in length. Example skin type AFP polypeptides include sAFP1, sAFP2, sAFP3, sAFP4, sAFP5, sAFP6, sAFP7, sAFP8, F2 and 11-3.

Preferred Skin type AFPs of the invention are optionally assessed by examining the secondary structure of the polypeptides. In one class of embodiments, the polypeptides of the invention, as measured by circular dichroism, are between about 55% and about 75% α helical, more typically about 60% and 70% α helical, often about 65% α helical. Certain polypeptides of the invention optionally do not meet this criteria, e.g., where the polypeptide is a fusion protein which includes subsequences which are unrelated to a skin-type AFP. Fusion proteins comprising skin-type AFP subsequences are a feature of the invention. Preferred fusion proteins include a skin-type AFP subsequence and a subsequences from GST, keyhole limpet hemanocyanin and other common fusion polypeptide domains.

Skin type AFPs of the invention are optionally defined by their immunological characteristics. Preferred AFPs bind polyclonal antibodies raised against any (or all) of the polypeptides sAFP1, sAFP2, sAFP3, sAFP4, sAFP5, sAFP6, sAFP7, sAFP8, F2 and 11-3. Preferred polypeptides also bind to polyclonal antibodies raised against any one (or all) of the polypeptides sAFP1, sAFP2, sAFP3, sAFP4, sAFP5, sAFP6, sAFP7, sAFP8, F2 and 11-3, where the polyclonal antisera are subtracted with a liver-type polypeptide such as HPLC 6 or HPLC 8.

Isolated polypeptides are optionally present as purified lyophilized powders, in aqueous solutions (e.g., comprising water, for instance with salts at physiological concentrations), in recombinant cells, plants, animals, bacteria, prokaryotes, cell extracts and the like. The polypeptides are optionally present in foods such as ice cream or frozen yoghurt.

Isolated skin-type antifreeze polypeptides are preferably encoded by a coding nucleic acid (RNA or DNA) which hybridizes to a skin type antifreeze nucleic acid selected from the group consisting of sAFP1, sAFP2, sAFP3, sAFP4, sAFP5, sAFP6, sAFP7, sAFP8, F2 and 11-3 in a northern blot or Southern blot under high stringency wash conditions. An example high stringency wash condition is 0.015M NaCl at 72° C. Preferably, the skin-type antifreeze polypeptides do not significantly hybridize to liver type AFP coding nucleic acids, such as a nucleic acid encoding HPLC6 (e.g., PENCE 17, see FIG. 7) under the same high stringency wash conditions. The liver type AFP nucleic acid does not significantly hybridize to a skin-type nucleic acid if the signal to noise ratio on a Southern or northern blot is reduced 75% or more as compared to the binding of a fully complementary skin type AFP. For example, if a radiolabeled liver type probe and a radiolabeled skin type probe with the same specific activity are used to probe duplicate Southern blots, and an autoradiogramii shows that the liver specific probe signal has less than 25% the intensity of the skin specific probe after a high stringency wash, then the detected nucleic acid is a skin specific nucleic acid.

In another class of embodiments, the invention provides nucleic acids such as expression vectors which encode a skin type AFP. The expression vector encoded AFPs typically have the same properties as the isolated polypeptides described above and herein.

In a preferred embodiment, the expression vector encodes a first skin type intracellular antifreeze nucleic acid which first nucleic acid hybridizes to a second skin type antifreeze nucleic acid selected from the group consisting of sAFP1, sAFP2, sAFP3, sAFP4, sAFP5, sAFP6, sAFP7, and sAFP8 in a Southern or northern blot under high stringency wash conditions of 0.015M NaCl at 72° C., wherein the first nucleic acid does not significantly hybridize to a pkenc 17 nucleic acid under the same wash conditions, wherein the first nucleic acid encodes a skin type antifreeze polypeptide, with the properties described above and herein. For example, the expression vector can encode a nucleic acid which codes for a polypeptide selected from the group of polypeptides corresponding to sAFP1, sAFP2, sAFP3, sAFP4, sAFP5, sAFP6, sAFP7, and sAFP8.

In one class of embodiments, the invention provides recombinant cells comprising a skin-type antifreeze nucleic acid which encodes a skin type antifreeze polypeptide with the properties discussed above and herein. The cells typically express the skin-type AFP, but in certain embodiments, such as cells used in cloning, the cell does not express an AFP. Cells expressing the polypeptide are cold resistant, meaning they can tolerate colder temperatures than similar cells which do not express an AFP, and can more readily survive freezing. The cell is optionally a eukaryotic cell such as a plant, fungal or animal cell, or is optionally a prokaryotic cell such as a bacteria, or is optionally an archaebacterial cell.

In one class of embodiments, the invention provides methods of depressing the freezing point of an aqueous composition by adding skin type AFPs to the aqueous composition. Preferred skin type AFPs of the invention depress the freezing point of an aqueous solution in a concentration-dependent manner, e.g., as measured thermal hysteresis. The aqueous composition can be a solution such as a water-salt solution, an intracellular compartment of a cell, or a food stuff such as soft serve "frozen" yoghurt or ice cream.

In another class of embodiments, the invention provides antibodies which specifically bind to a skin-type antifreeze polypeptides. Preferred antibodies are specific for skin type AFPs, and do not bind to liver AFPs.

The invention also provides skin-specific genes and promoters. It is now discovered that the genomic sequences for the genes 11-3 and F2 include related promoters which preferentially direct expression of the associated skin-type nucleic acid in the skin of Winter Flounder. The genes also direct lower levels of expression in other flounder tissues, and are active in other organisms, particularly other fish. The sequences of the 11-3 and F2 genes which occur within 1000 bases of the coding sequences of the 11-3 and F2 genes comprise promoter elements which direct expression in the skin, e.g., of the winter flounder. Preferred promoters comprise sequences which are similar to the 5' and/or 3' nucleic acids flanking the coding regions of these genes, and optionally include the intronic and coding regions of these genes as well. Similar sequences bind to these nucleic acids under stringent hybridization conditions. Preferred promoter elements include the nucleic acid subsequences GAATAAAT, CATCAGGACTCAAACACTTTTCACTGTC-GACCACTCAG (SEQ ID NO:4) CTGCAAAA and AATAAA, which are perfectly conserved between the 11-3 and F2 promoters (see, SEQ ID NOS: 31 and 33 respectively). Promoters which include all of these elements are skin-type promoters, even if the promoter nucleic acids do not hybridize to the 11-3 or F2 promoters under stringent conditions.

BRIEF DESCRIPTION OF THE DRAWINGS

FIG. 2 shows an amino acid sequence comparison of representative type 1 antifreeze polypeptides. HPLC-6 (SEQ ID NO:39 ) is a major liver-type AFP from winter flounder. sAFP1 (SEQ ID NO:16), is a representative skin-type AFP from winter flounder. See also, SEQ ID NOS: 16, 18, 20, 22, 24, 26, 28 30).

FIG. 4 shows the amino acid sequence of flounder skin-type AFPs. The amino acid sequences were deduced from cDNA and genomic clones. The amino acid sequences were also determined directly from AFPs using amino acid sequencing methods.

FIG. 5 shows a sequence comparison of the "pseudogene" F2 and skin AFP cDNA clone S3 (the nucleic acid encoding sAFP2). Identical nucleotides are shown as hyphens in S3. The two sequences encode an identical polypeptide shown above the nucleotide sequences. The two major transcription start sites, as determined by primer extension in FIG. 6, are indicated by ^. Sequence before the transcription start sites are shown in small letters. The position of an intron is indicated by an arrowhead. The putative TFIID binding site, aataat, the oligonucleotide for primer extension, and the polyadenylation site AATAAA are underlined. See also, SEQ ID NOS: 16, 18, 20, 22, 24, 26, 28, and 30.

FIG. 6 shows the DNA sequence of F2. See also, Davies and Gauthier (1992), supra. The transcribed sequence is shown as full size letters while the 5' flanking sequences and intron are shown as small letters. The initiation codon ATG and the terminal codon TAA are highlighted. The TFIID binding motif (aataaat), oct-1 binding site (ctgcaaaa) and polyadenylation signal AATAAA are underlined. See also, SEQ ID NO: 32.

FIG. 7 shows the DNA sequence of the probe pkenc 17 (SEQ ID NO: 33).

FIG. 8 shows the DNA sequence of 11-3 (see also, Davies and Gauthier (1992), supra) (SEQ ID NO: 33). The transcribed sequence is shown as full size letters while the 5' flanking sequences and intron are shown as small letters. The initiation codon ATG and the terminal codon TAA are highlighted. The TFIID binding motif (aataaat), oct-1 binding site (ctgcaaaa) and polyadenylation signal AATAAA are underlined.

FIG. 10 shows the nucleic acid sequences corresponding to sAFP1 (S4)-sAFP5 (S2) (SEQ ID NO: 15–24). Start and stop codons are highlighted.

FIG. 11 shows the nucleic acid sequences corresponding to sAFP6 (L4)-sAFP8 (S6) (SEQ ID NO: 25–30). Start and stop codons are highlighted.

FIG. 14 shows the peptide sequences of altered synthetic skin AFPs.

DEFINITIONS

Figure 1A:
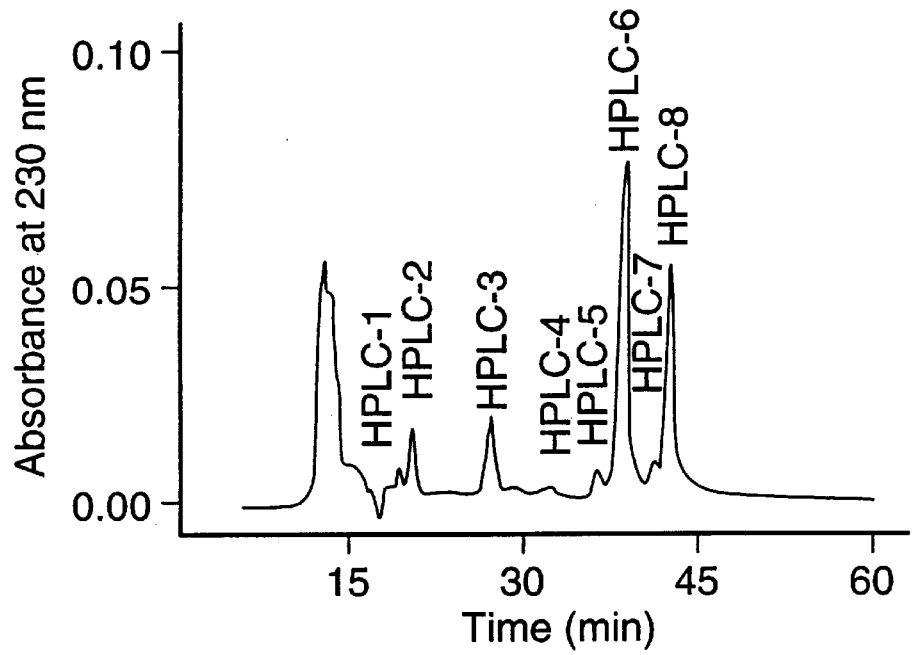
FIG. 1 shows a reverse phase HPLC profiles of flounder AFPs. (A) Serum AFP; (B) Skin AFP. Sephadex G75 purified antifreeze from sera (A) and skin scrapings (B) were fractionated on a Bondclone 10 C18 column (2.1×30 cm), flow rate 4.5 ml/min with a 20–40% acetonitrile, 0.1 % trifluoroacetic acid gradient.

Although any methods and materials similar or equivalent to those described herein can be used in the practice or testing of the present invention, the preferred methods and materials are described. For purposes of the present invention, the following terms are defined below.

The term "antibody" refers to a polypeptide substantially encoded by an immunoglobulin gene or immunoglobulin genes, or fragments thereof. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplar immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist e.g., as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$ 1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see, *Fundamental Immunology*, Third Edition, W. E. Paul, ed., Raven Press, N.Y. (1993), which is incorporated herein by reference, for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

The terms "isolated" or "biologically pure" refer to material which is substantially or essentially free from components which normally accompany it as found in its naturally occurring environment. The isolated material optionally comprises material not found with the material in its natural environment. For instance, "isolated" AFPs naturally found in fish skin optionally include heterologous cell components, food materials and the like.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. A nucleic acid "encodes" another nucleic acid where it is the same as the specified nucleic acid, or complementary to the specified nucleic acid.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" includes a recombinant expression cassette which includes a nucleic acid which encodes a polypeptide which can be transcribed and translated by a cell. A "recombinant expression cassette" is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the recombinant expression cassette portion of the expression vector includes a nucleic acid to be transcribed, and a promoter. In some embodiments, the expression cassette also includes, e.g., an origin of replication, and/or chromosome integration elements. A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. The promoter also includes distal enhancer or repressor elements which can be located as much as several thousand base pairs from the start site of transcription. A "constitutive" promoter is a promoter which is active Linder most environmental conditions and states of development or cell differentiation. An "inducible" promoter responds to an extracellular stimulus.

The term "recombinant" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means, for example under the control of a heterologous promoter.

The term "heterologous" when used with reference to a nucleic acid indicates that the nucleic acid comprises two or more subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene.

The term "subsequence" in the context of a particular nucleic acid or polypeptide sequence refers to a region of the nucleic acid or polypeptide equal to or smaller than the particular nucleic acid or polypeptide. Certain polypeptides of the invention optionally include multiple domains derived from more than one polypeptide. For example, Fusion proteins comprising skin-type AFP subsequences are a feature of the invention. Preferred fusion proteins include a skin-type AFP subsequence (typically at least 30%, generally 50%, often 70%, preferably about 80%, occasionally 90%, most preferably 100% of a give skin type AFP), and a subsequences from a common fusion moiety useful for increasing the immunogenicity or facilitating purification of the fusion. "Stringent hybridization" and "Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier; N.Y. Generally, highly stringent hybridization and wash conditions are selected to be about 5° C. lower than the thermal melting point ($T_m$) for the specific sequence at a defined ionic strength and ph. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, supra for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4–6×SSC at 40° C. for 15 minutes. In general, a signal to noise ratio of 2× (or higher) than that observed for an unrelated probe in the particular hybridization assay indicates detection of a specific hybridization. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "identical" in the context of two nucleic acid or polypeptide sequences refers to the residues in the two sequences which are the same when aligned for maximum correspondence over a specified comparison window. When percentage of sequence identity is used in reference to proteins or peptides it is recognized that residue positions which are not identical often differ by conservative amino acid substitutions, where amino acids residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., USA).

Methods of alignment of sequences for comparison are well known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) *Gene,* 73: 237–244 and Higgins and Sharp (1989) *CABIOS* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible. silent variation of the nucleic acid. One of skill will recognize that each codon in a nucleic acid (except AUG, which is ordinarily the only codon for methionine) can be modified to yield a functionally identical molecule. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

"Skin-type AFPs" are a family of closely related antifreeze proteins, found, for example, in Winter Flounder. The Skin-type AFPs are alanine-rich polypeptides which typically comprise an MDAP motif (or more preferably an MDAPA motif) at their N terminus and which typically comprise an internal AATAAAAKAAA sequence, although some conservative substitutions of these sequences are also contemplated as discussed above and herein. The skin-type AFPs share common epitopes which are recognized by antibodies, and share the common ability to inhibit the formation of ice crystals, thereby depressing the freezing point of aqueous solutions.

Skin type promoters are promoters which direct expression of a nucleic acid in the skin of a Winter Flounder. The promoter also typically directs lower levels of expression of the nucleic acid in tissues other than the skin. The promoter is also active in organisms besides Winter Flounder, particularly fish species related to the Flounder. The promoter is optionally heterologous, i.e., the promoter is optionally used to direct expression of nucleic acids unrelated to skin type AFPs, e.g., where high levels of expression of a nucleic acid in the skin are desirable. The promoter is optionally used as part of an AFP gene, where it is typically in its naturally occurring relationship with the AFP coding sequence.

DETAILED DISCUSSION OF THE INVENTION

In the present invention, a new family of "skin-type" AFPs and their corresponding nucleic acids were isolated. The skin-type AFP genes are ubiquitously expressed in all tissues examined in the Winter Flounder, with high levels in the exterior tissues such as skin, scales, fin and gills. Structurally, skin-type AFP lacks both pre and pro sequences, demonstrating an intracellular role for the polypeptides in freeze protection. Distinct antifreeze polypeptides were isolated from the skin of the winter flounder, *Pleuronectes americanus*, by gel filtration and reverse phase high performance liquid chromatography. In parallel, several cDNA clones were isolated from a skin cDNA library. Both protein and DNA sequence analyses indicate that flounder skin contains several distinct, but homologous, alaninie-rich AFPs termed skin-type AFPs.

In AFP-producing fish species previously studied, AFPs are synthesized in the liver and secreted into the blood circulation. These liver-type AFPs function by lowering the plasma freezing temperature to prevent fish from freezing in ice-laden sea water. The skin AFP genes of the invention encode polypeptides without the signal peptide, indicating that they function as intracellular proteins. The analysis of the HPLC profile (FIG. 1A) of plasma AFP did not reveal the presence of any skin-type AFP in the circulation, further supporting an intracellular role for skin type AFPs.

A cytosolic AFP plays a significant antifreeze role by providing a barrier to ice crystal passage or growth through the skin. Valerio et at. (1992) *J. Exp. Biol.* 164: 135–151 found that isolated skin from winter flounder was a significant barrier to ice crystal growth. It is now clear that this protective phenomenon is due to the skin-type AFPs herein. The high levels of skin-type AFP message in exterior tissues (about 20% of total skin mRNA) reflects the ability of high concentrations of AFP to achieve effective cellular protection from freezing. In many interior tissues, the expression is relatively low, but significant, at about 1–10% of the skin level. These tissues may already be protected by circulating plasma AFPs which are produced in liver. Low levels of intracellular AFPs may also have other physiological roles in these tissues.

Figure 3:
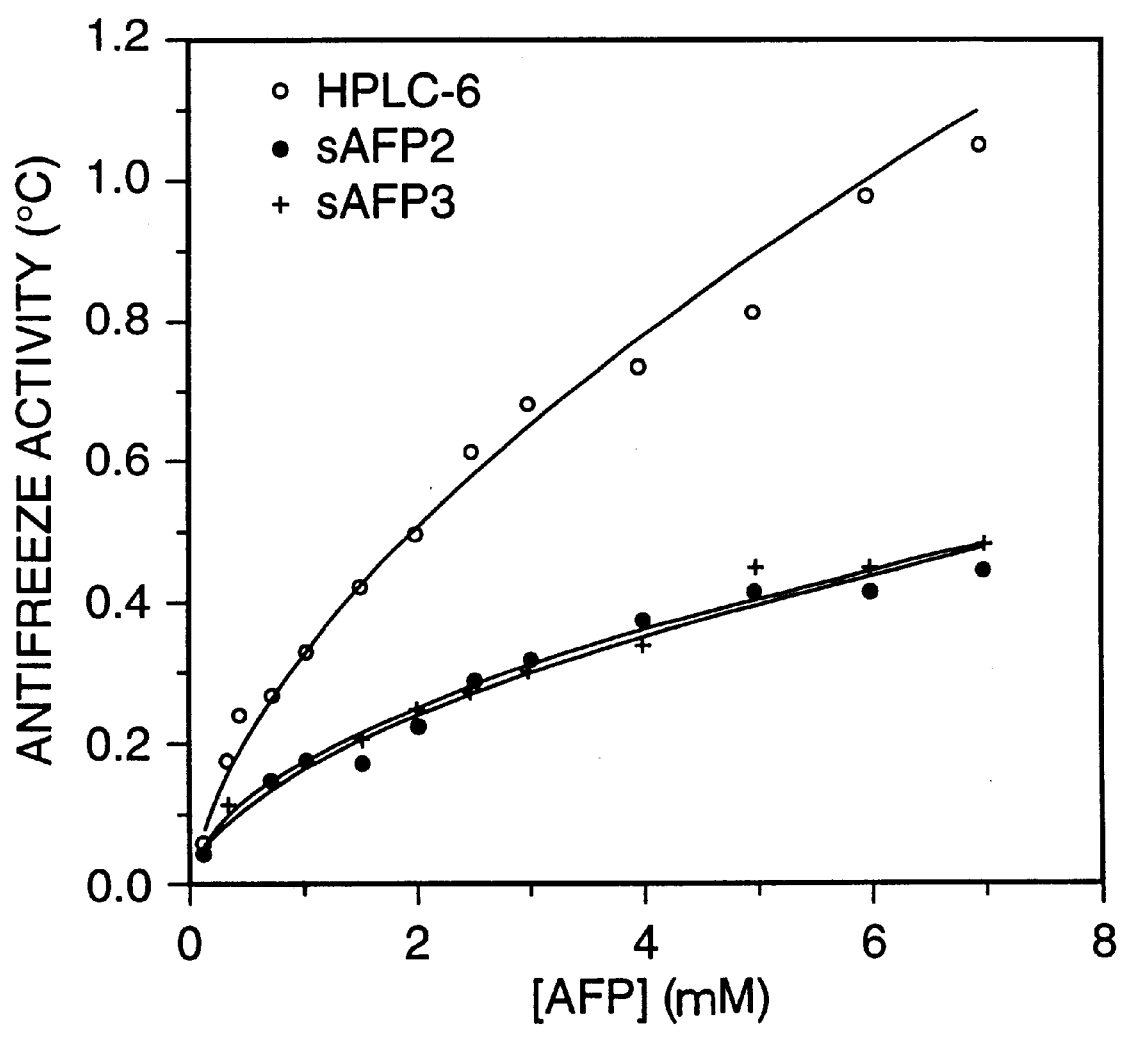
FIG. 3 shows the concentration dependence of the antifreeze activities of AFPs isolated from flounder serum and skin. The AFPs are the major serum AFP (HPLC-6) and skin AFPs, sAFP2 and sAFP3.
Figure 9:
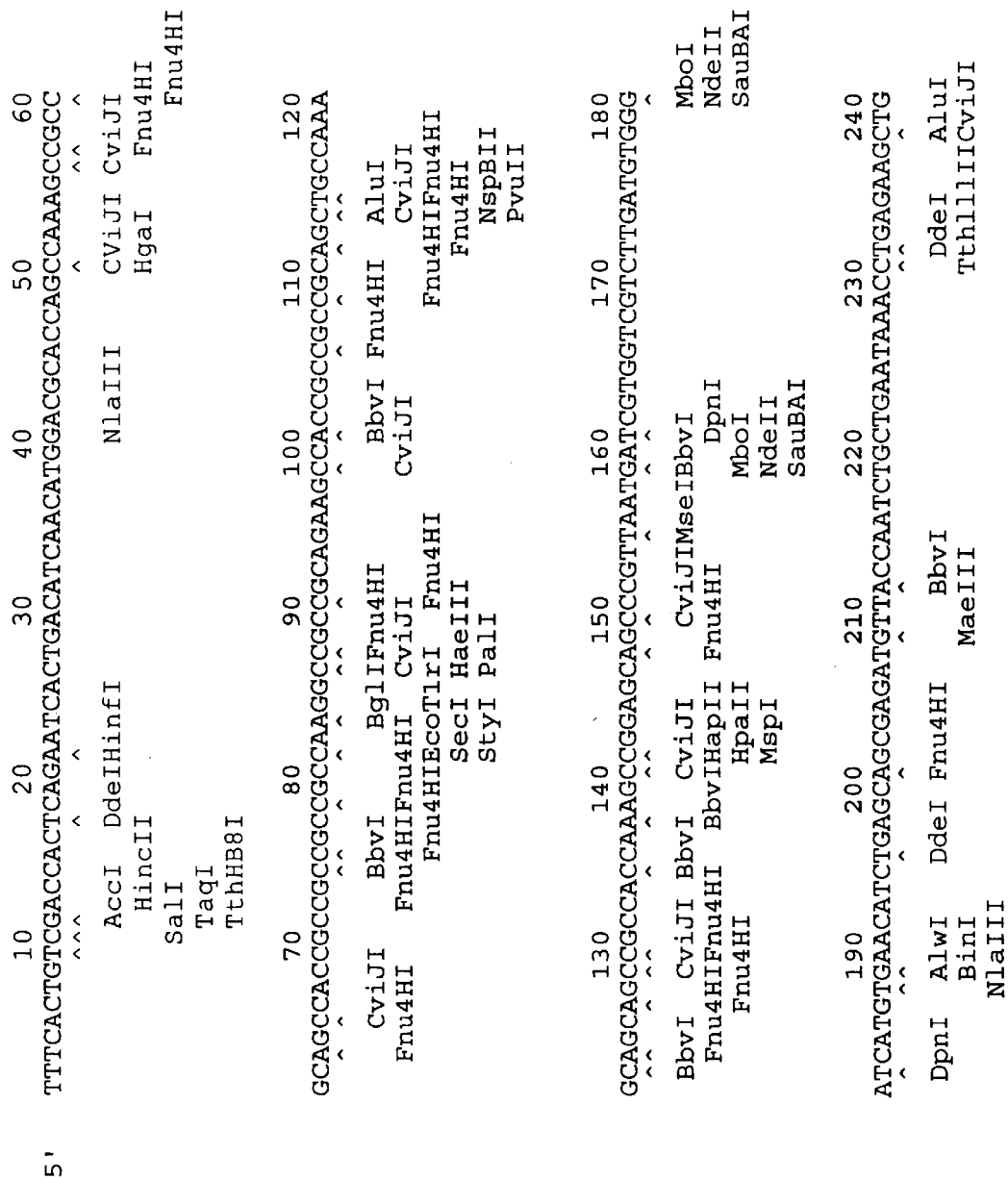
FIG. 9 shows a restriction map for an sAFP2 nucleic acid (SEQ ID NO: 17.

The activities of the skin AFPs fall within the range of fish AFP activities in general (Kao et al. (1986) *Can. J. Zool.* 64: 578–582). However, they are not as high as those of serum AFP from winter flounder (FIG. 3). The skin AFPs lack several residues that, in the serum AFP, are known to contribute to antifreeze activity (Wen et al. (1992) Biophys. J. 63: 1659–1662). Most of the skin AFPs have Thr residues as potential ice crystal interaction sites where their helical repeats are generally -Thr -$X_7$-(instead of -Thr-$X_2$-Asn/Asp-$X_5$- as in liver type AFPs). The identification of specific ice-binding motifs in the crystal structure of flounder serum HPLC-6 consisting of Thr/Asp or of Thr/Asn/Leu (Sicheri et al. (1995) Nature 375: 427–431) further defines the functional implications of the skin type Thr AFP sequence. Single Thr residues are incomplete motifs which bind more weakly to ice than the liver type AFP binding site -Thr-$X_2$-Asn/Asp-$X_5$-.

It is clear that both liver and skin-type AFP genes belong to multigene families. Most, if not all, of the liver genes are tandemly repeated with regular spacing (Scott et al. (1985) *Proc. Natl. Acad. Sci. USA.* 82: 2613–2617). The skin-type AFP genes (30–40 copies) are also linked. There are about 70–80 copies of AFP genes including both the liver- and skin-type in the winter flounder genoine. The liver-type AFP genes are expressed predominantly in liver and to a much lesser extent in intestine. Consistent with this, no liver-type AFP cDNA clones were isolated from the skin cDNA library. In contrast, the skin AFP genes are ubiquitously expressed. Since there are 30–40 copies of skin AFP genes, some of these skin-type genes may be specifically expressed in certain tissues. The discovery of non-liver AFP genes in the winter flounder suggests variants with different structures and tissue specificities occur in the AFP gene families of other AFP-producing species, particularly those species producing different types of AFPs. For example, like the winter flounder, the ocean pout (*Macrozoarces americanus*), which synthesizes type III AFPs, has an AFP multigene family (Hew et al., 1988) and expresses AFP mRNAs predominantly in the liver but also in many non-liver tissues (Gong et al. (1992) *Can. J. Zool.* 70: 810–814).

This invention represents the first report that two distinct types of AFP are present within the same species, and represents the first report of the skin type AFP genes and polypeptides.

Making AFP Nucleic Acids and Polypeptides

Several specific nucleic acids encoding skin-type AFP polypeptides are described herein. These nucleic acids can be made using standard recombinant or synthetic techniques. Given the nucleic acids of the present invention, one of skill can construct a variety of clones containing functionally equivalent nucleic acids, such as nucleic acids which encode the same polypeptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory, Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acid compositions of this invention, whether RNA, cDNA, genomic DNA, or a hybrid of the various combinations, are isolated from biological sources or synthesized in vitro. The nucleic acids of the invention are present in transformed or transfected cells, in transformed or transfected cell lysates, or in a partially purified or substantially pure form.

In vitro amplification techniques suitable for amplifying sequences for use as molecular probes or generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook et al. (1989) *Molecular Cloning—A Laboratory Manual* (2nd Ed) Vol. 1–3; and Ausubel, as well as Mullis et al., (1987) U.S. Pat. No. 4,683,202; PCR *Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989)*Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990)*Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039.

Oligonucleotides for use as probes, e.g., in in vitro AFP nucleic acid amplification methods, or for use as nucleic acid probes to detect AFP nucleic acids are typically synthesized chemically according to the solid phase phosphoramidite triester method described by Beaucage and Caruthers (1981), *Tetrahedron Letts.,* 22(20):1859–1862, e.g., using an automated synthesizer, e.g., as described in Needham-VanDevanter et al. (1984) *Nucleic Acid Res.,* 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chron.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook et al. (1989) *Molecular Cloning—A Laboratory Manual* (2nd Ed) Vol. 1–3; Innis, Ausbel, Berger, Needhain VanDevanter and Mullis (all supra).

Polypeptides of the invention can be synthetically prepared in a wide variety of well-known ways. Polypeptides of relatively short size are typically synthesized in solution or on a solid support in accordance with conventional techniques. See, e.g., Merrifield (1963) *J. Am. Chem. Soc.* 85:2149–2154. Various automatic synthesizers and sequencers are commercially available and can be used in accordance with known protocols. See, e.g., Stewart and Young (1984) *Solid Phase Peptide Synthesis,* 2d. ed., Pierce Chemical Co. Polypeptides are also produced by recombinant expression of a nucleic acid encoding the polypeptide followed by purification using standard techniques.

Screening for AFP Nucleic Acids and the Use of AFP Nucleic Acids as Molecular Probes The nucleic acids of the invention are useful as molecular probes, in addition to their utility in encoding the polypeptides described herein. A wide variety of formats and labels are available and appropriate for nucleic acid hybridization, including those reviewed in Tijssen (1993) *Laboratory Techniques in biochemistry and molecular biology—hybridization with nucleic acid probes* parts I and II, Elsevier, New York and Choo (ed) (1994) *Methods In Molecular Biology Volumne 33—In Situ Hybridization Protocols* Humana Press Inc., New Jersey (see also, other books in the Methods in Molecular Biology series); see especially, Chapter 21 of Choo (id) "Detection of Virus Nucleic Acids by Radioactive and Nonisotopic in Situ Hybridization".

For instance, PCR is routinely used to detect AFP nucleic acids in biological samples (see, Innis, supra for a general description of PCR techniques). Accordingly, in one class of embodiments, the nucleic acids of the invention are used as PCR primers, or as positive controls in PCR reactions for the detection of AFPs in a biological sample such as a cold water fish, or genetically engineered organism comprising an AFP. Briefly, nucleic acids encoded by the nucleic acid constructs of the invention are used as templates to synthetically produce oligonucleotides of about 15–25 nucleotides with sequences similar or identical to a selected AFP nucleic acid subsequence. The oligonucleotides are then used as primers in PCR reactions to detect AFP nucleic acids in biological samples such as an uncharacterized fish skin extract. The nucleic acids of the invention (i.e., a nucleic acid corresponding to the region to be amplified) are also used as amplification templates in separate reactions to determine that the PCR reagents and hybridization conditions are appropriate.

Other methods for the detection of nucleic acids in biological samples using nucleic acids of the invention include Southern blots, northern blots, in situ hybridization (including Fluorescent in situ hybridization (FISH), reverse chromosome painting, FISH on DAPI stained chromosomes, generation of Alphoid DNA probes for FISH using PCR, PRINS labeling of DNA, free chromatin mapping and a variety of other techniques described in Choo (supra)). A variety of automated soild-phase detection techniques are also appropriate. For instance, very large scale immobilized polymer arrays (VLSIPS™) are used for the detection of nucleic acids. See, Tijssen (supra), Fodor et al. (1991) *Science,* 251: 767–777 and Sheldon et al. (1993) *Clinical Chemistry* 39(4): 718–719.

Skin-type AFP nucleic acids hybridize to probes based upon the nucleotide sequences herein. In particular, skin AFPs typically contain an MDAPA N terminal sequence, and their 5' untranslated sequences are homologous. Using sAFP2 as example, an oligonucleotide complementary to the 5' sequence (antisense) can be used as probe to screen for skin AFPs in a skin cDNA library. sense: 5'-CTC AGA ATC ACT GAC ATC AAA ATG GAC GCA CCA GCC-3' antisense: 3'-GAG TCT TAG TGA CTG TAG TTT TAC CTG CGT GGT CGG-5'

Typically, the probe is used to screen a cDNA or genomic library generated from fish skin using standard techniques (genomic libraries and cDNA libraries are also publicly available from sources known to skilled investigators). Library members (typically bacterial clones or bacterial phage) which hybridize to the antisense oligonucleotide under stringent conditions are selected as skin-type AFP candidates. The library members are then sequenced and compared to other skin type AFPs to verify that they are skin-type AFPs. Note that nucleic acids corresponding to the MDAP or more preferably the MDAPA sequence can be used to discriminate between skin type AFP nucleic acids and liver type AFP nucleic acids, because skin type AFPs typically include the MDAPA motif, whereas liver type AFPs typically do not.

PCR primers can also be designed using the above probes to amplify AFP nucleic acids. For example, a primer corresponding to the MDAP sequence can be used in conjunction with a carboxyl terminal probe, or with a poly T probe which binds to an mRNA poly A sequence. The MDAP primer in conjunction with a poly T primer specifically amplifies reverse-transcribed skin-type AFP mRNA.

Making Conservative Modifications of the Nucleic Acids and Polypeptides of the Invention One of skill will appreciate that many conservative variations of the sequences disclosed yield an essentially identical AFP. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties (see, the definitions section, supray, are also readily identified as being highly similar to a disclosed amino acid sequence, or to a disclosed nucleic acid sequence which encodes an amino acid. Such conservatively substituted variations of each explicitly disclosed sequence are a feature of the present invention.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97, Roberts et al. (1987) *Nature* 328:731–734 and Sambrook, Innis, Ausbel, Berger, Needham VanDevanter and Mullis (all supra).

Most commonly, polypeptide sequences are altered by changing the corresponding nucleic acid sequence and expressing the polypeptide. However, polypeptide sequences are also optionally generated synthetically using commercially available peptide synthesizers to produce any desired polypeptide (see, Merrifield, and Stewart and Young, supra).

One of skill can select a desired nucleic acid or polypeptide of the invention based upon the sequences provided and upon knowledge in the art regarding AFPs generally. The physical characteristics and general properties of AFPs are known to skilled practitioners. The specific effects of some mutations in AFPs are known. Moreover, general knowledge regarding the nature of proteins and nucleic acids allows one of skill to select appropriate sequences with activity similar or equivalent to the nucleic acids and polypeptides disclosed in the sequence listings herein. The definitions section herein describes exemplar conservative amino acid substitutions.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, thermal hysteresis, hydrophobicity, susceptibility to proteolysis, or the tendency to aggregate are all assayed according to standard techniques.

Cloning and Expressing AFPs

Once an AFP nucleic acid is isolated and cloned, one may express the nucleic acid in a variety of recombinantly engineered cells known to those of skill in the art. Examples of such cells include bacteria, yeast, plant, filamentous fungi, insect (especially employing baculoviral vectors), and mammalian cells. It is expected that those of skill in the art are knowledgeable in the numerous expression systems available for cloning and expression of nucleic acids.

In brief summary, the expression of natural or synthetic nucleic acids encoding a skin-type AFP is typically achieved by operably linking a nucleic acid encoding the polypeptide of interest to a promoter (which is either constitutive or inducible), and incorporating the construct into an expression vector. The vectors can be suitable for replication and integration in prokaryotes, eukaryotes, or both. Typical cloning vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See, e.g., Sambrook and Ausbel (both supra).

Expression in Prokaryotes

To obtain high levels of expression of a cloned nucleic acid, expression vectors which typically contain a strong promoter to direct transcription, a ribosome binding site for translational initiation, and a transcription/translation terminator. For example, as described herein, the polypeptides encoded by skin type AFPs, which are useful, e.g., in protecting cells against cold, and as antigenic reagents, are optionally expressed in bacterial cells such as *E. coli*. Examples of regulatory regions suitable for this purpose in *E. coli* are the promoter and operator region of the *E. coli* tryptophan biosynthetic pathway as described by Yanofsky, C., 1984, *J. Bacterlol.*, 158:1018–1024 and the leftward promoter of phage lambda ($P_L$) as described by Herskowitz and Hagen, 1980, *Ann. Rev. Genet.*, 14:399–445. The inclusion of selection markers in DNA vectors transformed in bacteria such as *E. coli* is also useful. Examples of such markers include genes specifying resistance to ampicillin, tetracycline, or chloramphenicol. See, Sambrook, Ausbel, and Berger for details concerning selection markers, e.g., for use in *E. coli*. Expression systems for expressing polypeptides are available using *E. coli*, Bacillus sp. (Palva, I. et at., 1983, *Gene* 22:229–235; Mosbach, K. et al., *Nature*, 302:543–545) Lactobacillus (ChagnaLud et al. (1992) *Can. J. Microbiol*. 38: 69–74; Teuber (1993) *Food Reviews International* 9(3): 389–409) *Streptococcus thermophilus* (Mollet et al. (1993) *Journal of Bacteriology* 175(14): 4315–4324; Akahoshi et al. U.S. Pat. No. 4,970,083; Klaver et al. U.S. Pat. No. 4,938,973) and Salmonella. *E. coli* systems are the most common, and best defined expression systems and are, therefore, typically preferred. However, in contexts were it is desirable to express AFPs in bacteria used in food production, such as Lactobacillus (used, e.g., in yoghurt and ice cream production), these systems are preferred. Shuttle systems for transferring vectors between *E. coli* and Lactobacillus are known. See, Chagnaud et al. and Teuber et al., both id.

Polypeptides produced by prokaryotic cells often require exposure to chaotropic agents for proper folding. During purification from, e.g., *E. coli*, the expressed protein is optionally denatured and then renatured. This is accomplished, e.g., by solubilizing the bacterially produced polypeptides in a chaotropic agent such as guanidine HCI. The polypeptide is then renatured, either by slow dialysis or by gel filtration. See, U.S. Pat. No. 4,511,503.

An example of expression of a skin type AFP in bacteria is provided in the Examples section at example 6.

Expression in Eukaryotes

Methods of transfecting and expressing genes in eukaryotic cells are also known in the art. An example of expression of a skin type AFP in eukaryotes is provided in the Examples section at example 7.

Transformation of yeast found in frozen dough or bread is of particular use because yeast expressing skin type AFPs have high viability upon thawing, retaining the ability to naturally leaven the dough. Thus, in one preferred embodiment, the AFPs of the invention are expressed in yeast. See, e.g., Sherman et al. (1982) *Methods in Yeast Genetics*, Cold Spring Harbor Laboratory. Examples of promoters for use in yeast include GAL1,10 (Johnson and Davies (1984) *Mol. Cell. Biol.* 4:1440–1448) ADH2 (Russell et al. (1983) *J. Biol. Cheni.* 258:2674–2682), PH05 (*EMBO J.* (1982) 6:675–680), and MFα1 (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209). A multicopy plasmid with selective markers such as Leu-2, URA-3, Trp-1, and His-3 is also commonly used. A number of yeast expression plasmids like YEp6, YEp13, YEp4 can be used as expression vectors. An AFP of interest can be fused to any of the promoters in various yeast vectors. The above-mentioned plasmids have been fully described in the literature (Botstein et al. (1979) *Gene* 8:17–24; Broach, et al. (1979) *Gene,* 8:121–133).

Two procedures are commonly used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in Beggs (1978) *Nature* (London) 275:104–109, and Hinnen et al. (1978) *Proc. Natl. Acad. Sci. USA* 75:1929–1933. The second procedure does not involve removal of the cell wall. Instead the cells are treated, e.g., with lithium chloride or acetate and PEG and put on selective plates (Ito, et al. (1983) *J. Bact.* 153:163–168).

The polypeptides of interest are isolated from yeast (or other cells) by lysing the cells and applying standard protein isolation techniques to the lysates. The polypeptides of this invention are purified to substantial purity by standard techniques well known in the art, including selective precipitation with such substances as ammonium sulfate, column chromatography, immunopurification methods, and others. See, for instance, Scopes (1982) *Protein Purification: Principles and Practice* Springer-Verlag New York. The monitoring of the purification process is accomplished by using Western blot techniques or radioimmunoassays or other standard immunoassay techniques, or by monitoring the protein directly, e.g., by coomassie blue or silver-stain polyacrylamide gel electrophoresis.

Yet another embodiment is the introduction of AFPs into other cells destined for frozen storage, such as tissue or cell depositories. Illustrative of cells improved by the production of AFPs are cells of fungal, plant, insect or vertebrate (e.g., fish or mammalian) origin. Particularly preferred uses include the transformation of fragile and expensive cell lines such as hybridomiia cell lines and tissue culture cell lines. Transducing such cells with AFP nucleic acids is accomplished by various known means. These include calcium phosphate precipitation, fusion of the recipient cells with bacterial protoplasts containing the DNA, treatment of the recipient cells with liposoines containing the DNA, DEAE dextran, receptor-mediated endocytosis, electroporation, micro-injection of the DNA directly into the cells, incubating viral vectors containing target nucleic acids which encode polypeptides of interest with cells within the host range of the vector, calcium phosphate transfection, and many other techniques known to those of skill. See, e.g., *Methods in Enzymology,* vol. 185, Academic Press, Inc., San Diego, Calif. (D. V. Goeddel, ed.) (1990) or M. Krieger, *Gene Transfer and Expression—A Laboratory Manual,* Stockton Press, New York, N.Y., (1990) and the references cited therein, as well as Sambrook and Ausbel. The culture of cells used in conjunction with the present invention, including cell lines and cultured cells from tissue or blood samples is well known in the art. Freshney (*Culture of Animal Cells, a Manual of Basic Technique,* third edition Wiley-Liss, New York (1994)) and the references cited therein provides a general guide to the culture of cells. See also, Kuchler et al. (1977) *Biochemical Methods in Cell Culture and Virology,* Kuchler, R. J., Dowden, Hutchinson and Ross, Inc.

As indicated above, the expression vector e.g., a plasmid, which is used to transform the host cell, preferably contains nucleic acid sequences to initiate transcription and sequences to control the translation of the encoded polypeptide. These sequences are referred to generally as expression control sequences. When the host cell is of insect or mammalian origin, illustrative expression control sequences are obtained from the SV-40 promoter (*Science* (1983) 222:524–527), the CMV I.E. Promoter (*Proc. Natl. Acad. Sci.* (1984) 81:659–663) or the metallothionein promoter (*Nature* (1982) 296:39–42). The cloning vector containing the expression control sequences is cleaved using restriction enzymes and adjusted in size as necessary or desirable and ligated with DNA coding for the polypeptide of interest by known means.

As with yeast, when higher animal host cells are employed, polyadenlyation or transcription terminator sequences from known mammalian genes are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al. (1983) *J. Virol.* 45: 773–781).

Additionally, gene sequences to control replication in a particular host cell are incorporated into the vector. An example of such sequences are those found in bovine papilloma virus type-vectors. See, Saveria-Campo (1985), "Bovine Papilloma virus DNA a Eukaryotic Cloning Vector" in *DNA Cloning Vol. II a Practical Approach* Glover (ed) IRL Press, Arlington, Virginia pp. 213–238.

Sequences controlling eukaryotic gene expression have been extensively studied. Promoter sequence elements include the TATA box consensus sequence (TATAAT), which is usually 20 to 30 base pairs (bp) upstream of the transcription start site. In most instances the TATA box is required for accurate transcription initiation. By convention, the start site is called +1. Sequences extending in the 5' (upstream) direction are given negative numbers and sequences extending in the 3' (downstream) direction are given positive numbers. These sequences are optionally incorporated into the expression vector as part of a characterized heterologous promoter. In the construction of heterologotis promoter/structural gene combinations, the promoter is preferably positioned about the same distance from the heterologous transcription start site as it is from the transcription start site in its natural setting. As is known in the art, however, some variation in this distance can be accommodated without loss of promoter function.

In one particularly preferred embodiment, the AFPs of the invention are expressed in plant cells, conferring cold resistance to the transformed plant. This has clear value to farmers and other crop producers in cold and temperate climates for the protection of valuable crops such as citrus fruits, tomatoes and the like. For expression in plants, a recombinant expression vector will contain, in addition to an AFP sequence, a plant promoter region, a transcription initiation site (if the sequence to be transcribed lacks one), and a transcription termination sequence arraigned in an expression cassette. Unique restriction enzyme sites at the 5' and 3' ends of the cassette are typically included to allow for easy insertion into a pre-existing vector.

In plants, further upstream from the TATA box, at positions −80 to −100, there is typically a promoter element with a series of adenines surrounding the trinucleotide G (or T). See, Messing et al., in *Genetic Engineering in Plants*, pp. 221–227 (Kosage, Meredith and Hollaender, eds. 1983).

Other sequences conferring tissue specificity, response to environmental signals, or maximum efficiency of transcription are also found in the promoter region. Such sequences are often found within 400 bp of transcription initiation size, but may extend as far as 2000 bp or more from the start site of transcription.

The particular promoter used in the expression cassette in plants is a noncritical aspect of the invention. Any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids. See, Herrara-Estrella et al. (1983), *Nature,* 303:209–213. Viral promoters include the 35S and 19S RNA promoters of cauliflower mosaic virus. See, Odell et al. (1985) *Nature,* 313:810–812. Possible plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer, (1988) *EMBO J.* 7:3315–3327.

Polyadenylation aids in expression of cDNA in plant cells. Polyadenylation sequences include, but are not limited to the Agrobacterium octopine synthase signal (Gielen et al. (1984) *EMBO J.,* 3:835–846) and the nopaline synthase signal (Depicker et al. (1982) *Mol. and Appl. Genet,* 1:561–573. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow an a medium containing the particular antibiotic.

Plant expression vectors can be microinjected directly into plant cells by use of micropipettes to mechanically transfer the recombinant DNA. Crossway (1985) *Mol. Gen. Genetics,* 202:179–185. The genetic material may also be transferred into the plant cell using polyethylene glycol. See, Krens, et al. (1982) *Nature,* 296, 72–74. Another method of introduction of expression vectors is high velocity ballistic penetration by small particles with the nucleic acid either within the matrix of small beads or particles, or on the surface. See, Klein, et al. (1987) *Nature,* 327, 70–73.

Yet another method of introduction in plants is the fusion of protoplasts with other entities, either minicells, cells, lysosomes or other fusible lipid-surfaced bodies. See, Fraley, et al. 1982 *Proc. Natl. Acad. Sci. USA,* 79, 1859–1863. Expression vectors may also be introduced into the plant cells by electroporation. See, Fromm et al. (1985) *Pro. Natl Acad. Sci. USA,* 82:5824. In this technique, plant protoplasts are electroporated in the presence of plasmids containing the expression vector. Electrical impulses of high field strength reversibly permeabilize biomembranes, allowing the introduction of the plasmids. Electroporated plant protoplasts reform the cell wall, divide, and regenerate.

Cauliflower mosaic virus (CaMV) may be used as a vector for introducing the expression vector into plant cells. See, Hohn et al. (1982) *Molecular Biology of Plant Tumors* Academic Press, New York, pp.549–560, and Howell, U.S. Pat. No. 4,407,956. Typically, the CaMV viral DNA genoine is inserted into a parent bacterial plasmid, creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

The most preferred vector-mediated method of introducing the expression vector into plant cells is to infect a plant cell with *Agrobacterium tunic faciens* or *A. rhizogenes* previously transformed with the gene. Under appropriate conditions known in the art, the transformed plant cells are grown to form shoots or roots, and develop further into plants. Heterologous genetic sequences can be introduced into appropriate plant cells, by means of the Ti plasmid of *A. turniefaciens* or the Ri plasmid of *A. rhizogenes*. The Ti or Ri plasmid is transmitted to plant cells on infection by Agrobacterium and is stably integrated into the plant genome. See, J. Schell (1987) *Science,* 237: 1176–1183 and Hoekema, et al. (1983), *Nature,* 303:179–189. All plant cells which can be transformed by Agrobacterium and from which whole plants can be regenerated can be transformed according to the present invention to produce transformed intact plants which contain the desired DNA. See, Hooykas-Van Slogteren et al. (1984), *Nature,* 311:763–764; de la Pena et al. (1987) *Nature* 325:274–276; Rhodes et al. (1988) *Science* 240:204–207; Shimainoto et al. (1989) *Nature* 338:274–276. Plant regeneration from cultured protoplasts is described in Evans et al., Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. I, 1984, and Vol. III, 1986.

Some suitable plants for transformation by the expression vectors of the invention include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyarn us, Lycopersicon, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, Apium, and Datura, including sugarcane, sugar beet, cotton, fruit trees, and legumes.

Making and using Antibodies to Skin-Type Polypeptides

In one embodiment, antibodies are provided which specifically bind to skin-type polypeptides. Antibodies can be raised to the polypeptides of the present invention, including individual, allelic, strain, or species variants, and fragments thereof, both in their naturally occurring (full-length) forms and in recombinant forms. Additionally, antibodies can be raised to these polypeptides in either their native configurations or in non-native configurations. Anti-idiotypic antibodies may also be generated. Many methods of making antibodies are known to persons of skill. One of skill will recognize that many variations upon the following methods are known.

a. Antibody Production

A number of immunogens may be used to produce antibodies which specifically bind skin type AFPs. Recombinant or synthetic polypeptides of 10 amino acids in length, or greater, selected from sub-sequences of the skin type polypeptide provided in SEQ ID NOS 1–6, 9 and 15–30 are preferred polypeptide immunogens for the production of monoclonal or polyclonal antibodies. A particularly preferred polypeptide comprises the polypeptide subsequence MDAP. In one class of preferred embodiments, an immunogenic peptide conjugate is also included as an immunogen. Naturally occurring polypeptides may also be used either in pure or impure form.

Recombinant polypeptides are expressed in etikaryotic or prokaryotic cells and purified using standard techniques, or purified directly from Winter Flounder using the techniques described herein. The polypeptide, or a synthetic version thereof, is then injected into an animal capable of producing antibodies. Either monoclonal or polyclonal antibodies are generated for subsequent use, e.g., in immunoassays to measure the presence and quantity of the polypeptide.

Methods of producing polyclonal antibodies are known to those of skill in the art. In brief, an immunogen, preferably a purified polypeptide, a polypeptide coupled to an appropriate carrier (e.g., GST, keyhole limpet hemanocyanin, etc.), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan (1991) *Current Protocols in Immunology* Wiley/Greene, N.Y.; and Harlow and Lane (1989) *Antibodies: A Laboratory Manual* Cold Spring Harbor Press, N.Y., which are incorporated herein by reference.

Antibodies, including binding fragments and single chain recombinant versions thereof, against predetermined fragments of skin-type AFPs can be raised by immunization of animals, e.g., with conjugates of the fragments with carrier proteins as described above. Typically, the immunogen of interest is a peptide of at least about 3 amino acids, more typically the peptide is 5 amino acids in length, preferably, the fragment is 10 amino acids in length and more preferably the fragment is 15 amino acids in length or greater. The peptides are optionally coupled to a carrier protein (e.g., as a fusion protein), or are recombinantly expressed in an immunization vector. Antigeneic determinants on polypeptides to which antibodies bind are typically 3 to 10 amino acids in length.

In addition to polypeptide domains, fusion partners for intracellular AFP subsequences other than polypeptides are also a feature of the invention. Lipids, modified polypeptides, carbohydrates and other moieties are optionally linked to AFP polypeptide subsequences of the invention, e.g., to improve the immunogenicity of the resulting fusion molecule, or to facilitate purification of the fusion molecule. For example, avidin or biotin can be added to an AFP to facilitate purification of the fusion molecule by binding of biotin to avidin. Similarly, antibodies or antibody-ligands can be fused to AFP subsequences for purification by binding of antibody to the corresponding ligand. Many recombinant and chemical techniques for fusion of polypeptide subsequences to additional molecules are known.

Monoclonal antibodies are optionally prepared from cells secreting the desired antibody. These antibodies can be screened for binding to normal or modified polypeptides, or screened for agonistic or antagonistic activity, e.g., activity mediated through a skin type AFP (e.g., thermal hysteresis). Specific monoclonal and polyclonal antibodies will usually bind with a $K_D$ of at least about 0.01 $\mu$M, more usually at least about 50 $\mu$M, and most preferably at least about 1 $\mu$M or better.

In some instances, it is desirable to prepare monoclonal antibodies from various mammalian hosts, such as mice, rodents, primates, humans, etc. Description of techniques for preparing such monoclonal antibodies may be found in, e.g., Stites et al. (eds.) *Basic and Clinical Immunology* (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495–497. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate host. The polypeptides and antibodies of the present invention are used with or without modification, and include chimeric antibodies such as humanized murine antibodies.

Other suitable techniques involve selection of libraries of recombinant antibodies in phage or similar vectors. See, Huse et al. (1989) "Generation of a Large Combinatorial Library of the Immunoglobulin Repertoire in Phage Lambda," *Science* 246: 1275–1281; and Ward, et al. (1989) *Nature* 341: 544–546.

Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen et al. (1989) *Proc. Natl. Acad. Sci. USA* 86: 10029–10033.

The antibodies of this invention can also be used for affinity chromatography in isolating skin type AFPs, or for the identification of AFPs in a biological mixture. Columns can be prepared, e.g., with the antibodies linked to a solid support, e.g., particles, such as agarose, Sephadex, or the like, where a cell lysate is passed through the column, washed, and treated with increasing concentrations of a mild denaturant, whereby purified AFPs are released.

The antibodies can be used to screen expression libraries for skin-type AFP expression products. Usually the antibodies in such a procedure will be labeled with a moiety allowing easy detection of presence of antigen by antibody binding.

Antibodies raised against AFPs can also be used to raise anti-idiotypic antibodies. These are useful for making antibodies with antifreeze properties.

b. Immunoassays

AFPs can be detected or measured by a variety of immunoassay methods, including western blots and ELISA analysis. For a review of immunological and immunoassay procedures in general, see Stites and Terr (eds.) 1991 *Basic and Clinical Immunology* (7th ed.). The immunoassays can be performed in any of several configurations, e.g., those reviewed in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; Harlow and Lane, supra; Chan (ed.) (1987) *Immunoassay*: A Practical Guide Academic Press, Orlando, Fla.; Price and Newman (eds.) (1991) *Principles and Practice of Immunoassays* Stockton Press, N.Y.; and Ngo (ed.) (1988) *Non-isotopic Immunoassays* Plenum Press, N.Y.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled AFP or a labeled anti-AFP antibody. Alternatively, the labeling agent may be a third moiety, such as another antibody, that specifically binds to the antibody/AFP complex, or to a modified capture group (e.g., biotin) which is covalently linked to the AFP or anti-AFP antibody.

In a preferred embodiments, the labeling agent is an antibody that specifically binds to the capture agent (anti-AFP). Such agents are well known to those of skill in the art, and most typically comprise labeled antibodies that specifically bind antibodies of the particular animal species from which the capture agent is derived (e.g., an anti-idiotypic antibody). Thus, for example, where the capture agent is a mouse derived anti- AFP antibody, the label agent is optionally a goat anti-mouse IgG, i.e., an antibody specific to the constant region of the mouse antibody.

Other proteins capable of specifically binding immunoglobulin constant regions, such as streptococcal protein A or protein G may also be used as the label agent. These proteins are normal constituents of the cell walls of streptococcal bacteria. They exhibit a strong non-immunogenic reactivity with immunoglobulin constant regions from a variety of species. See, generally Kronval, it al., *J. Immunol.*, 111:1401–1406 (1973), and Akerstrom, et al., *J. Immunol.*, 135:2589–2542 (1985).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 5° C. to 45° C.

c. Generation of Pooled Antisera for Use in Immunoassays

AFPs that specifically bind to or that are specifically immunoreactive with an antibody generated against a defined immunogen, such as an immunogen consisting of an amino acid sequence selected from the group of amino acid sequences from SEQ ID No 1–6, 9 and 15–30 is determined in an immunoassay. The immunoassay uses a polyclonal antiserum which was raised one of the polypeptides given in the sequence listings (the immunogenic polypeptide), preferably sAFP1, sAFP2, aAFP3, sAFP4, sAFP5, sAFP6, sAFP7, sAFP8, F2 or 11-3. This antiserum is selected to have low crossreactivity against other AFPs such as liver AFPs, and any such crossreactivity is removed by immunoabsorbtion prior to use in the immunoassay (e.g., by immunosorbtion of the antisera with Liver type polypeptides such as HPLC-6 and HPLC-8).

In order to produce antisera for use in an immunoassay, a polypeptide selected from the group of polypeptides listed in SEQ ID NO 1–6, 9 and 15–30 is isolated as described herein. For example, a recombinant AFP, such as sAFP1, sAFP2, aAFP3, sAFP4, sAFP5, sAFP6, sAFP7, sAFP8, F2 or 11-3, is optionally produced in a cell line, or isolated from Winter Flounder fish skin as described in the examples. An inbred strain of mice such as balb/c is immunized with the selected AFP using a standard adjuvant, such as Freund's adjuvant, and a standard mouse immunization protocol (see Harlow and Lane, supra). Alternatively, a synthetic polypeptide derived from the sequences disclosed herein and conjugated to a carrier protein is used as an immunogen. Polyclonal sera are collected and titered against the immunogic polypeptide in an immunoassay, for example, a solid phase immunoassay with the immulnogen immobilized on a solid support. Polyclonal antisera with a titer of $10^4$ or greater are selected and tested for their cross reactivity against liver type AFPs using a competitive binding immunoassay such as the one described in Harlow and Lane, supra, at pages 570–573. Preferably two liver type AFPs (e.g., HPLC-6 and HPLC-8) are used in this determination in conjunction with more than one skin type AFP. In conjunction with skin-type AFP, Liver AFPs are used as competitors to identify antibodies which are specifically bound by a skin-type AFP. The competitive inhibitors can be produced as recombinant proteins and isolated using standard molecular biology and protein chemistry techniques as described herein, or isolated from fish liver using standard techniques.

Immunoassays in a competitive binding format are typically used for crossreactivity determinations. For example, the immunogenic polypeptide is immobilized to a solid support. Liver type AFPs added to the assay compete with the binding of the antisera to the immobilized antigen. The ability of the liver AFPs to compete for binding of the antisera to the immobilized protein is compared to the immunogenic polypeptide. The percent crossreactivity for the above proteins is calculated, using standard calculations. Those antisera with less than 10% crossreactivity with liver AFPs are selected and pooled. The cross-reacting antibodies are then removed from the pooled antisera by immunoabsorbtioni with the liver type AFPs.

The immunoabsorbed and pooled antisera are then used in a competitive binding immunoassay as described herein to compare a second "target" AFP to the immunogenic AFP. In order to make this comparison, the two AFPs are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immnuniogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test AFP is specifically bound by the antisera elicited by the immunogenic AFP.

Thermal Hysteresis and Related Tests

The effect of the AFPs of the invention on the freezing of aqueous solutions can be assayed using a variety of techniques. Skin type AFPs alter the size of ice crystals formed upon freezing, and the temperature at which water freezes, both in a concentration-dependent manner. Thus, the activity of skin type AFPs are typically tested using one or both of two tests. The first test is an assay for a reduction in crystal size upon rapid freezing. This is performed by dropping serial dilutions of an aqueous solution containing a known amount of AFP onto a cold block of metal and measuring the size of the resulting ice crystals, and recrystallizing ice crystals scraped from the surface of the block. This is the "splat" test, as described, e.g., by Knight et at. (1988) Cryobiology 25: 55–60; Knight and Dugman (1986) Cryobiology 23: 256–262; Knight et al. (1984) Nature 308:295–296 and Warren et al. U.S. Pat No. 5,118,792.

The preferred method of measuring the activity of a skin type AFP is to measure the thermal hysteresis (the difference between the melting and freezing temperatures) of an aqueous solution containing the AFP. This can be done by performing a serial dilution of the AFP-containing aqueous solution, followed by cooling the solution gradually and monitoring the freezing point of the solution. Typically, this is performed using commercially available equipment designed specifically for this purpose, such as nanoliter osmoineter. See, Kao et al. (1986) Can. J. Zool. 64:578–582. A preferred osmometer is the Clifton Nanoliter Osmoineter (Clifton Technical Physics, Hartford, N.Y.). Instructions for using the equipment to perform thermal hysteresis are available from the manufacturer. See alvo, Chakrabartty et al. (1989) J. Biol. Cheni. 264: 11313–11316, for a preferred procedure for measuring thermal hysteresis.

Uses for the AFPs of the Invention

As described herein, the AFPs of the invention depress the freezing point of aqueous solutions in a concentration dependent manner. Accordingly, the AFPs of the invention are generally useful in protecting solutions against freezing. This improves the shelf-life of many refrigerated foods, making the foods more palatable. In the case of cold viscous liquids such as soft-serve ice creams and frozen yogurt, various emulsifiers are used to keep the components of the liquid in solution. The AFP, when added, inhibits ice recrystalization during cold storage, improving the texture and palatability of the food.

Cells which express the AFPs of the invention are more cold-tolerant than counterpart cells which do not express AFPs. This is due to freezing point depression of the intracellular compartment, and prevention of cellular dehydration and osmotic damage. Thus, the AFPs of the invention are used to improve the cold tolerance of bacteria, cell cultures, plants and animals. This has many useful commercial applications in medicine, agriculture and aquaculture. For instance, cold resistant plants have a longer growing season in temperate and northern climates than their ordinary counterparts. This allows for higher crop yields, and protects crops against unanticipated early frosts. Essentially any crop grown in a temperate or northern climate is improved by increased cold resistance. In particular, citrus crops such as oranges, grapefruit, lemons and tangerines benefit from cold-resistance, as do tomatoes, tobacco, potatoes, legumes and the like.

In a preferred embodiment, the AFPs are expressed in commercially farmed fish such as catfish and talipia to improve the freeze tolerance of the fish. In this regard, AFP promoters are also useful to target expressed recombinant AFPs to the skin of animals in general and fish in particular.

Transgenic fish are generated by microinjection or electroporation of fertilized eggs. Electroporation of fish sperm is also used. See, Fletcher et al. (1988) *Can. J. Fish Aquatic Sci.* 45: 352–357, and Gong and Hew (1995) "Transgenic Fish in Aquaculture and Developmental Biology" in *Current Topics in Developmental Biology* 30: 178–214 for a discussion of fish transformation techniques.

In a preferred embodiment, AFPs are expressed in medically valuable cell lines such as hybridoma lines to improve the freeze tolerance of the cell lines.

AFPs also have certain antibacterial properties, providing a means of unwanted reducing bacteria in foods such as recombinant fruits expressing AFPs, and in blended food stuffs such as ice creams. This improves shelf life, food quality, and makes such products safer for consumption.

EXAMPLES

The following examples are provided by way of illustration only and not by way of limitation. Those of skill will readily recognize a variety of noncritical parameters which can be changed or modified to yield essentially similar results.

Materials and Methods

The following materials and methods were used in examples 1–7 below.

Structural analysis of skin AFP—Purified skin AFPs from Reverse Phase HPLC were used for amino acid analysis, protein sequencing and mass spectroscopy. Both amino acid analysis and protein sequencing were performed by the Biotechnology Service Centre, Hospital for Sick Children, Toronto, and mass spectrometry by the Carbohydrate Centre, University of Toronto, Toronto. For amino acid analysis, the samples were hydrolyzed in 6 N HCl at 110° C. for 24 hr and analyzed using the Waters Picotag System. Because of the blockage of the N-terminus methionine, skin AFPs were pretreated with cyanogen bromide (in 5% formic acid, 24 hr, with 200 fold molar excess of CNBr) prior to protein sequencing in a Porton Gas Phase Sequencer.

DNA sequencing—Double strand DNA sequencing was performed by dideoxynucleotide chain termination using the 17 DNA sequencing kit according to the manufacturer's instructions (Pharmacia, Montreal, Quebec, Canada). Each clone contained about 240–300 bp cDNA insert and complete sequences were obtained by sequencing from both ends using SK and T7 primers.

Primer extension—A 22mer oligonucleotide, 5'-GGCTGGTGCGTCCATGTTGATG-3' (SEQ ID NO: 8), complementary to the region starting 7 bases upstream of the ATG codon in sAFP2 (clone S3) (FIG. 5), was synthesized by the Biotechnology Service Centre, Toronto. The oligonucleotide was labelled using γ32P-ATP by T4 DNA kinase. The primer extension experiment was carried out as described by Sambrook et al., (1989).

Genomic Southern blot hybridization—Genomic DNA was isolated from a testis collected from a single fish by the method of Blin et al. (1976) *Nucleic Acid. Res.* 3: 2303–2308. Briefly, about 0.4 g of testis was digested with proteinase K in 50 mM Tris, pH 8, 100 mM EDTA, 0.5% SDS overnight at 50° C. The mixture was then extracted extensively with phenol/chloroform. The aqueous phase was dialyzed against TE (10 mM Tris, pH8; 1 mM EDTA) and high molecular weight DNA was collected by the addition of NaCl to 0.1 M and 2 volumes of ethanol. Restriction-digested genomic DNA was separated by electrophoresis on a 0.7% agarose gel. The gel was soaked in 0.4 M NAOH, 0.6 M NaCl for 30 min. and blotted onto a Hybond membrane (Amersham) in the same solution. Hybridization was performed as previously described (Gong et al. (1992) *Can. J. Zool.* 70: 810–814).

Northern blot hybridization—Total RNAs from selected tissues were extracted as stated above. Total RNAs were separated by formaldehyde agarose gel electrophoresis and Northern blot hybridization was performed as previously described (Gong et al. (1992) *Can. J. Zool.* 70: 810–814). The relative levels of AFP mRNAs were estimated by densitometric scanning of autoradiograins using ScanJet 3P (Hewlett Packard) and analysis using a computer program (NIH Image 1.52).

Example 1

Isolation and Characterization of Skin-type AFP From Skin Scrapings

HPLC purification and subsequent characterization of skin-type AFP was performed to determine the protein composition and sequence of several skin-type AFPs directly, and to investigate the hysteresis properties of naturally synthesized skin-type AFP.

Winter flounder (*Pleuronectus americanus*) were collected from Conception Bay, Newfoundland, Canada. Several tissues were removed and frozen in liquid nitrogen and stored at −70° C. before use. Winter flounder skin scrapings (46 g) were homogenized in 500 ml of 0.1 M $NH_4HCO_3$ using a Polytron homogenizer. After low speed centrifugation, the supernatant was lyophilized (1 g), redissolved and chromatographed in a Sephadex G75 column (2.5×80 cm) in 0.1M $NH_4HCO_3$. Active fractions, measured with a nanoliter osmometer, were pooled and rechromatographed once in the same column. The repurified materials, approximately 50 to 100 mg were further fractionated on a Bondclone 10 $C_{18}$ column (Phenomenex, Torrance, Calif.) using a 0.5% trifluoroacetic acid and acetonitrile gradient. Individual fractions were pooled and lyophilized.

Figure 1B:
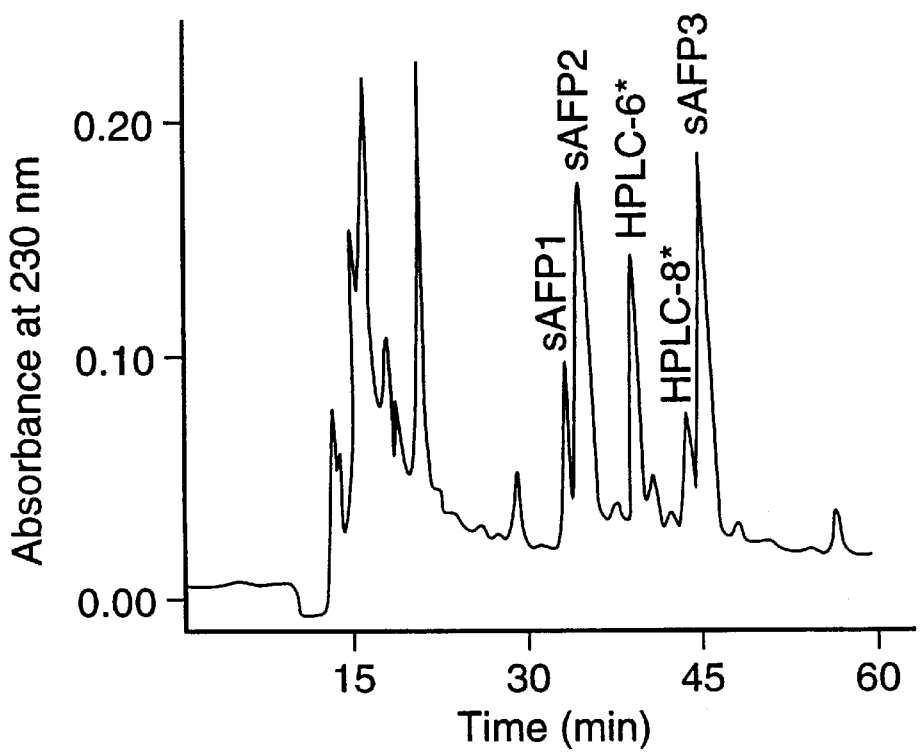

The HPLC profile of AFPs isolated from skin scrapings is shown in FIG. 1. The HPLC profile of gel filtration chromatography purified serum AFP is also included from comparison. The serum AFPs contain only two major components, i.e. HPLC-6 and HPLC-8 (FIG. 1A). Except for HPLC 5, 7 and 9, which represent post-translational modifications and minor serum AFPs, the other earlier elution peaks are not related to AFPs, as examined by amino acid analysis (Fourney et al. (1984) *Can. J. Zool.* 62: 28–33). However, the HPLC profile of AFP isolated from the skin scrapings was obviously more heterogenous and contained at least 5–6 components (FIG. 1B). The major skin AFPs are designated as sAFP1, sAFP2, sAFP3. HPLC-6* and HPLC-8* also appear in the HPLC profile, due to contamination of the skin scrapings with blood (HPLC 6* and HPLC 8* were verified to be the major liver-type AFPs HPLC 6 and HPLC 8 as shown below). In addition, there were several peaks which eluted early in the HPLC. These early elution peaks had minimal antifreeze activity. Furthermore, amino acid analysis of these materials showed the peaks were not significantly enriched with alanine and were not further investigated. HPLC-6* and HPLC-8* had retention times identical to the major liver type AFPs HPLC-6 and HPLC-8 respectively. Subsequent amino acid compositions and protein sequencing analyses confirmed that they were in fact HPLC-6 and HPLC-8, respectively and indicated contamination of the skin samples by blood.

Amino acid analyses indicated that the skin AFPs were also alanine rich, comprising 60.2% of alanine (comparable to 62.2% to HPLC-6 and HPLC-8). In addition, the skin AFPs contain methionine and proline, two amino acid residues absent in serum AFP, and are relatively low in leucine, aspartic acid and glutamic acids compared to HPLC-6 or HPLC-8. One of the skin AFPs (sAFP1) contains histidine, which is absent in serum AFP. The amino acid composition of the skin scrapings are shown in table 1.

TABLE 1

Amino Acid Composition of Antifreeze Polypeptides Isolated from Flounder Skin Scrapings

| | sAFP1 | sAFP2 | sAFP3 | HPLC-6* | HPLC-8* |
|---|---|---|---|---|---|
| Asx | 4.98(1) | 2.10(1) | 1.60(2) | 3.42(4) | 22.77(5) |
| Glx | 3.89(1) | 1.23(1) | 1.24(1) | 0.98(1) | 1.41(0) |
| Ser | 0.64 | — | — | 0.73(1) | 3.45(1) |
| Gly | 0.88 | 0.11(1) | — | — | — |
| His | 2.50(1) | — | — | — | — |
| Arg | 3.74(1) | 1.60(1) | 1.71(1) | 1.13(1) | 4.23(1) |
| Thr | 6.67(3) | 2.44(2) | 2.77(3) | 2.12(3) | 12.01(4) |
| Ala | 56.92(25) | 30.10(26) | 30.28(25) | 19.69(23) | 68.41(23) |
| Pro | 3.76(1) | 1.19(1) | 1.35(1) | 0.20 | 1.71 |
| Val | 0.45 | — | — | — | — |
| Met | 2.37(1) | 0.90(1) | 0.84(1) | — | — |
| Leu | 1.53 | 0.22 | -1.52(2) | 8.52(2) | — |
| Lys | 11.47(4) | 2.78(3) | 3.40(5) | 0.58(1) | 5.31(1) |

(The number in brackets are the number of aa residues deduced from cDNA sequence.
HPLC-6* and HPLC-8* correspond to liver-type HPLC-6 and HPLC-8, respectively (see,
Daviesetal.(1982);Pickettetal.(1984)Eur.J.Biochem.143:35–38).

Unlike the serum AFP (HPLC-6 and HPLC-8), the skin AFP N-termini were blocked. sAFP1, sAFP2 and sAFP3 were analyzed by Atmospheric Pressure Ionization Mass Spectroscopy (API-MS) to determine the nature of the blocking group. Based on their cDNA sequences to be described in the later sections, these peptides had $M_r$ of 3376.56, 3480.61 and 3482.67 respectively. API-MS analyses indicated that larger $M_r$ ions of 3419.06, 3480.61 and 3525.41 were present in sAFP1, sAFP2 and sAFP3 accordingly. The difference (+42 $M_r$) was consistent with the addition of an acetyl group at the N terminus. sAFP2, in addition, contained a minor $M_r$ of 3366.87 and indicating a slight contamination by sAFP7 ($M_r$ of 3324.46). The amino acid sequences were confirmed by protein sequencing after CNBr cleavage of the N-terminal methionine. Like the serum AFPs, skin AFPs also contain similar threonine 11 amino acid repeats.

Example 2

Measurement of Antifreeze Activity of Skin-type AFPs

The activity of a skin-type AFP can be measured using a nanoliter osmometer. Antifreeze activity was measured as thermal hysteresis (the difference between the melting and freezing temperatures), essentially following the procedure of Chakrabartty et al. (1989) *J. Biol. Chem.* 264: 11313–11316. Proteins were dissolved in 0.1 M NH$_4$HCO$_3$ and their concentrations were determined by duplicate amino acid analyses. Activity measurements were performed on a series of dilutions with concentrations ranging from 0.1 to 7.0 mM for each protein using a Clifton Nanoliter Osmometer (Clifton Technical Physics, Hartford, N.Y.). Prior to the series of measurements for each protein, measurements were made from 3 sample wells using buffer alone and their average gave the background hysteresis. For each dilution, measurements were made from 3 wells and the average was taken. The background hysteresis was then subtracted from this value in order to obtain the antifreeze activity.

In FIG. 3, activities of the skin AFPs plotted as a function of concentration form hyperbolic curves consistent with those typically observed for type I AFPs (Scott et al. (1987) *Eur. J. Biochem.* 168: 629–633; Chakrabartty et al. (1989) *J. Biol. Chem.* 264: 11313–11316; Wen et al. (1992) *J. Biol. Chem.* 267, 14102–14108) and most other fish AFPs (Kao et al. (1986) *Can. J. Zool.* 64: 578–582). The activity curve of the major serum AFP, HPLC-6, was in line with those previously obtained using a synthetic analogue of this protein (Chakrabartty et al. (1989) *J. Biol. Chem.* 264: 11313–11316) and a mixture of AFPs from flounder serum (Kao et al. (1986) *Can. J. Zool.* 64: 578–582) *Can. J. Zool.* 64: 578–582).

In contrast, the AFPs isolated from skin are less active. The skin AFPs displayed lower activities than the serum AFP in all but the lowest (0.1 mM) concentration measured and activity curves appeared to be approaching saturation plateaus at lower concentrations than the serum protein (FIG. 3). The curves for two of the skin AFPs, sAFP2 and sAFP3, were virtually coincident with activities less than half of that observed for HPLC-6.

Example 3

Isolation and Characterization of Skin AFP cDNA clones; Hybridization of Skin-Type AFP Nucleic Acids to Liver-type Probes Several skin type AFP cDNAs and genomic DNAs were cloned, sequenced and characterized to determine the structure and organization of the skin-type genes and gene products. Total RNA was isolated using the skin tissues containing scales and a dorsal fin from a single individual fish collected in winter by the acid guanidium thiocyanate-phenol-chloroform extraction method as originally described by Chomczynski et al. (1987) *Anal. Biochem.* 162: 156–159 and modified for fish tissues by Gong et al. (1992) *Can. J. Zool.* 70: 810–814. Poly A+RNA was then selected by oligo dT Sepharose as described by Sambrook et al. (1989). The cDNA library was constructed using the lambda Uni-ZAP XR vector system from Stratagene (La Jolla, Calif.). About 2.9×10$^6$ primary clones were obtained from 2 µg of poly A+RNA. The skin AFP cDNA clones were screened by hybridization using a liver AFP cDNA clone, pkenc 17 (see, FIG. 7), which encodes the most abundant serum AFPs component A or HPLC-6 (Pickett et al. (1984) *Eur. J. Biochem.* 143: 35–38).

When a small portion of the primary library was screened with pkenc at low stringency (0.3 M Na$^+$, 55° C.), approximately 20% of the clones were positive, indicating an abundance of AFP mRNA in skin. 14 independent clones were completely sequenced and 9 distinct DNA sequences encoding 8 AFPs, i.e. sAFP1 to sAFP8 were obtained (FIG. 4). The 14 cDNA clones are listed in parentheses following each protein sequence. The clones do not significantly hybridize to pkenc under stringent conditions. The cDNA clones encoding the same sAFP have identical nucleotide sequence except for P12 and S3 which have three single nucleotide substitutions.

All of the clones, except for P13 and S6, which encode additional C terminal sequences, share a greater sequence identity (91.7–99.2%) to each other than to the liver AFP DNA sequences (72.1–82.2%). Most of the skin AFP clones encode a short polypeptide of 37–40 amino acid residues, with one of the skin type AFPs (sAFP8), having 54 residues (FIG. 4). The encoded sAFPs are almost identical, with the few amino acid differences largely restricted to the last few residues at the C-terminal end of the polypeptides. In addition, unlike the liver-type AFP genes, which encode the secretory AFPs, the skin-type AFP genes encode mature polypeptides without pre and pro sequences.

DNA sequence comparisons indicate that the skin AFP clones are closely related to two previously identified genomic sequences, F2 and 11-3 (Davies et al. (1992) *Gene* 112: 171–178). Part of the F2 sequence is shown in FIG. 5. The sequence of 11-3, which is almost identical to that of F2 and, in the region shown in FIG. 5, had only 5 nucleotide changes and a 5 base deletion (Davies et al. (1992) *Gene* 112: 171–178). Due to the presence of in frame stop codons in the 5' upstream region corresponding to the pre sequence in the liver AFP gene and the lack of a typical TATA box in the putative promoter region, these two genes were previously assigned as pseudogenes (Davies et al. (1992) *Gene* 112: 171–178). As shown in FIG. 4, sAFP2 is identical to the protein encoded by the "pseudogene" F2 and is different from the AFP encoded by 11-3 by one amino acid. One of the cDNA clones encoding sAFP2 (S3), has only two nucleotide substitutions compared to F2 (FIG. 5). These substitutions occur only in the 3' untranslated region. Another cDNA clone encoding sAFP2 (P12), also has two nucleotide substitutions at different locations (data not shown). Alignment of the cDNA and the genomic sequences indicate that there is an intron between nucleotides 167 and 168. Therefore, it is now determined that both F2 and 11-3 code for functional genes in skin and other peripheral tissues.

In order to confirm the isolated clones contain full length coding sequences, and to map the transcription start site of the skin-type AFP genes, primer extension was carried out. There are two major extension products using skin total RNA as templates. The extension is 17 or 18 bp from the 5' end of S3 (sAFP2) cDNA clones. Only one extension product corresponding to the long extension product in the scales was detected using liver RNA as templates. The two extension products map the transcription start site at bases 130 and 131 of the F2 gene (FIG. 5). A putative TFIID binding motif AATAAAT is found at 25 nucleotides upstream of the first start site, further indicating that F2 and 11-3 are functional genes. These data also confirm that the skin AFP clones contain a full length coding sequence, without the signal peptide and pro sequences. The two extension products may indicate two transcriptional initiation sites for the skin-type AFP genes. Alternatively, because the primers we used hybridize to all skin AFP genes, the two extension products could be the result of genetic polymorphism.

Example 4

Multiple Copies of Skin-type AFP Genes in the Genome

Since 9 different skin AFP cDNA clones encoding 8 distinct skin-type AFPs were identified, it is clear that the skin-type AFP genes belong to a multigene family similar to the liver-type AFP genes. In order to characterize members of the family, a genomic blot hybridization was performed. Genomic DNA was isolated from the testis collected from a single individual fish and cut with four different restriction enzymes, Hind III, Eco RI, Sst I and Bam HI. Two identical blots were made and probed with the liver-type (pkenc 17) and skin-type (S3) AFP probes respectively. Both probes hybridize to multiple bands. The skin probe recognizes most, if not all, liver AFP fragments while the liver AFP probe only hybridized to a limited number of DNA fragments. Since most of the liver AFP genes are regular tandem repeats and most liver AFP fragments contain multiple copies of AFP genes (up to 40 copies), it is likely that even a weak hybridization from the skin probe produces a strong signal. The cross hybridization was also observed in the Northern blot analyses. Another possibility is that some skin-type AFP genes may be clustered together with the liver-type AFP genes. Many of the skin-type AFP genes are also linked, as indicated by the hybridization pattern in Bam HI-digested DNA, in which the skin-type AFP gene signals are restricted to two high molecular weight fragments (over 23 kb). These data, together with the identification of at least 9 distinct skin AFP cDNA sequences, unequivocally support the presence of a skin-type AFP multigene family.

The hybridization pattern of the liver probe is similar to the previously published genomic blot by Scott et al. (1985) *Proc. Natl. Acad. Sci. USA*. 82: 2613–2617 which estimated there were about 40 copies of AFP genes in the winter flounder genome. This estimation did not include the skin-type AFP genes. By comparison of the hybridization intensity of skin and liver AFP DNA fragments, the number of skin-type AFP genes is roughly the same as the number of liver-type AFP genes. Therefore, it the skin-type AFP genes constitute 30–40 copies in the flounder genome. As discussed herein, 9 different skin AFP cDNA clones encoding 8 distinct AFPs have been isolated and characterized. At the protein level, at least 3 different antifreeze polypeptides have been identified by reverse phase HPLC.

Example 5

Tissue Distribution of AFP Transcripts

The tissue distribution of AFP transcripts were previously examined using a liver cDNA probe in the winter flounder (Gong et al. (1992) *Can. J. Zool.* 70: 810–814). Since the hybridization was performed at a relatively low stringency, non-liver AFP transcripts were also detected due to cross hybridization. With the availability of the skin AFP probe, the tissue distribution of AFP mRNAs were re-examined using a high stringency wash condition (0.015 M NaCl, 72° C.). Experimenits in which the liver and skin cDNA clones were cross-hybridized indicated that this wash condition resulted in a minimal cross hybridization between the skin and liver genes. Total RNAs were isolated from selected tissues collected from a single fish and probed with the skin and liver AFP probes respectively. The skin-type AFP mRNAs were detected in all tissues examined, including the liver, stomach, intestine, heart, spleen, kidney, and were strongly expressed in the exterior tissues such as skin, scales, fin and gills. These last four tissues expressed similar levels of skin-type AFP mRNAs while the other tissues expressed 1–10% of the level found in these exterior tissues. As the AFP cDNA clones represent 20% of the clones in the skin cDNA library, AFP mRNAs are an abundant mRNA species in all tissues in the winter. In the exterior tissues, the level of AFP mRNAs are extraordinarily high.

The two types of AFP mRNAs can also be distinguished by their size, as the liver-type AFP mRNAs are typically larger than the skin-type, because the liver-type AFP genes contain approximately 132 additional nucleotides encoding the pre and pro sequences. In the liver, some cross hybridization of the skin probe to the extremely abundant liver-type AFP mRNAs which constitute about 0.5–1 % of total RNA (Pickett et al. (1983) *Biochim. Biophys. Acta* 739: 97–104) was observed. Nevertheless, the skin type AFP mRNAs was clearly detected. The expression of liver-type AFP mRNAs is restricted to liver and intestine, and the stomach. To compare the total levels of AFP mRNAs in the liver and skin tissues, a blot containing liver, scale and stomach total RNAs was hybridized with a mixture of liver and skin AFP probes which were mixed and labeled in the same reaction to ensure the same specific activity for the two probes. The level of scale AFP mRNA was about 10–20% of the liver level, indicating that the skin and other exterior tissues such as gills, are also major sites for the synthesis of AFPs. In comparison, the stomach mainly expressed the skin-type AFP mRNAs at a level of about 10% of that in scales.

To further demonstrate the presence of skin-type AFP mRNA in the liver, a more specific approach, primer extension, was employed using the skin AFP-specific oligonucleotide CATCAACATGGACGCACCAGCC (see, underlined region of FIG. 5; SEQ ID NO: 34). A clear extension signal from the liver RNA, which is identical to one of the two major extension signals from the scale RNA, was detected, indicating that the skin-type AFP mRNAs were present in the liver. The relative level of skin-type AFP mRNA in the liver, based on the intensity of the extension signals and inputs of RNA was estimated to be at least 100 fold lower than that observed in the scales, which has the highest expression level for the skin-type AFP genes. Liver RNA from Atlantic salmon, a species without the AFP genes, was used as a control. It has no detectable extension product, indicating the high specificity of the primer used.

Example 6

Intracellular Expression Using a Bacterial Expression Vector

Expression of the sAFP2 gene in bacteria is provided as an example. The nucleotide sequence of sAFP2 is shown in SEQ ID NO 17.

The pET system provided by Stratagene (La Jolla, Calif., USA) is used as an example cloning system expression vector. The pET plasmids are bacterial expression vectors under the control of a strong prokaryotic transcription signal, the bacteriophage T7 promoter. The target genes are cloned in pET plasmids and transformed into host cells in which a copy of T7 RNA polymerase gene is incorporated chromosomally (e.g. the commercially available *E. coli* strain BL21 DE3). Because the T7 polymerase gene is under the control of a lac operon (lac UV5), the expression of the target gene can thus be induced by the addition of IPTG.

For the initial expression of sAFP as native protein, the gene is cloned between the NdeI and BamHI sites of the pET3 expression vector from Stratagene, which contains a highly efficient ribosome binding site. Two specific oligos will be synthesized for PCR and cloning of sAFP into pET3. The 5'-primer will ensure that ATG codon is generated to produce unfused AFP proteins. The sequences of the two oligos are as follows,
5'oligo: CATATGGACGCACCAGCCAAAGCC (SEQ ID NO: 11)
3'oligo: GGATCCTTAACGGGCTGCTCCGGC (SEQ ID NO: 12)

These two oligos are used in a PCR reaction. The amplified fragment bearing NdeI site at 5' end and BamHI at 3' end is cut with NdeI and BamHI and cloned into NdeI/BamHI double restricted pET3. The recombinant plasmid is selected by conventional molecular cloning techniques (svee, Sambrook and Ausbel, supra). Intracellular expression is achieved by adding IPTG into the bacterial cultural medium. Once expressed, the recombinant AFP in bacteria is detected either using the nanoliter osmometer for activity measurement or using immunoblot with anti-AFP antibodies.

Example 7

Intracellular Expression Using Eukaryotic Expression Vectors

Numerous mammalian expression vectors, primarily based on viral promoters such as the SV40 early promoter, cytomegalovirus immediate early gene promoter pCMV, herpes simplex virus thymidine kinase promoter are available commercially (i.e.) Clontech, Palo Alto, Calif.). pCMV is used as an example to express sAFP in mammalian cells. The pCMVβ vector contains the viral promoter, an intron (splice donor/splice acceptor), polyadenylation signal from SV40, and a full length *E. coli* βgalactosidase with eukaryotic initiation signal. The vector produces high level of βgal expression. The Not I fragment carrying the βgalactosidase gene is replaced with an sAFP2 gene. Two oligos are synthesized for PCR and cloning of the sAFP gene into the pCMV vector (The underlined nucleotides represent NotI cleavage sites).
5'GCGGCCGCATGGACGCACCAGCCAAAGCC (SEQ ID NO: 13)
3'GCGGCCGCTTAACGGGCTGCTCCGGC (SEQ ID NO: 14)

The recombinant plasmid is introduced into mammalian cells using a known method such as transfection or electroporation. Once expressed, the presence of AFP is monitored by activity measurement using the nanoliter osmometer or by immunoblot with an AFP antibody.

Example 8

Expression of an Intracellular Antifreeze Fusion Protein

The glutathione-S-transferase (GST) fusion protein system was used for expression of skin AFPs in bacteria (Smith and Johnson (1988) *Gene* 67, 31–40). An expression construct, pGST-AFPS3, was made by ligation of the AFP DNA insert (EcoR I and Xho I fragment) from the cDNA clone S3 to the EcoR I site of pGEX-2T (Pharmacia). The correct reading frame after the ligation was confirmed both by restriction digestion and DNA sequencing.

Expression of GST fusion protein was performed as described previously (Gong and Hew (1994) *Biochem.* 33, 15149–15158). Briefly, pGST-AFPS3 was transformed into *Escherichia coli* DH5α. The expression of GST-AFP fusion protein was induced by addition of IPTG to a final concentration of 0.1 mM in a bacterial culture with an $OD_{600}$ at approximately 0.5. The presence of GST-AFP fusion protein was confirmed by SDS polyacrylamide gel electrophoresis.

The bacteria expressing GST-AFP fusion protein were collected 3 hours after IPTG induction and suspended in 15% sucrose/50 mM Tris, pH 8.3/2 mM EDTA. Lysozyme was added to the suspension to a final concentration of 5 mM /ml. The bacteria were then incubated for 5 min. at room temperature, Triton-X100 was added to a final concentration of 1% and the solution was sonicated for 1 min. After lysis, $MgCl_2$ and DNase I were added to final concentrations of 5 mM and 10 μg/ml, respectively. The lysate was then cleared by centrifugation in a microftige. The GST-AFP was present in the soluble fraction and was isolated from other bacterial proteins using glutathione sepharose 4B column as described by Smith and Johnson (1988), above.

Intracellular AFPs are less active than extracellular AFPs, as measured by the nanoliter osmometer. To show that the lower activity of the intracellular AFP is a result of polypeptide structure, rather than, e.g., protein isolation or modification, the activity of the GST-sAFP2 fusion protein was determined. The activity of sAFP2 and GST-sAFP2 is indistinguishable, suggesting that intracellular AFPs have lower activity due to their primary protein structure, despite similar helical content as compared to, e.g., HPLC-6. This also shows that the AFPs of the invention can be combined with unrelated proteins to make fusion molecules such as fusion proteins, without destroying the antifreeze activity of the AFP domain of the fusion molecule.

Antifreeze activity was measured as thermal hysteresis (difference between the melting and freezing temperatures) essentially following the procedure of Chakrabartty et al. (1989) *J. Biol. Chem.* 264, 11307–11312. Proteins were dissolved in 0.1 M $NH_4HCO_3$ and their concentrations were determined by duplicate amino acid analyses. Activity measurements were performed on a series of dilutions with concentrations ranging from 0.1 to 7.0 mM for each protein using a Clifton Nanoliter Osmometer (Clifton Technical Physics, Hartford, N.Y.). Prior to the series of measurements for each protein, measurements were made from 3 sample wells using buffer alone and their average gave the background hysteresis. For each dilution, measurements were made from 3 wells and the average was taken. The background hysteresis was then subtracted from this value in order to obtain the antifreeze activity.

Example 9

Figure 12A:
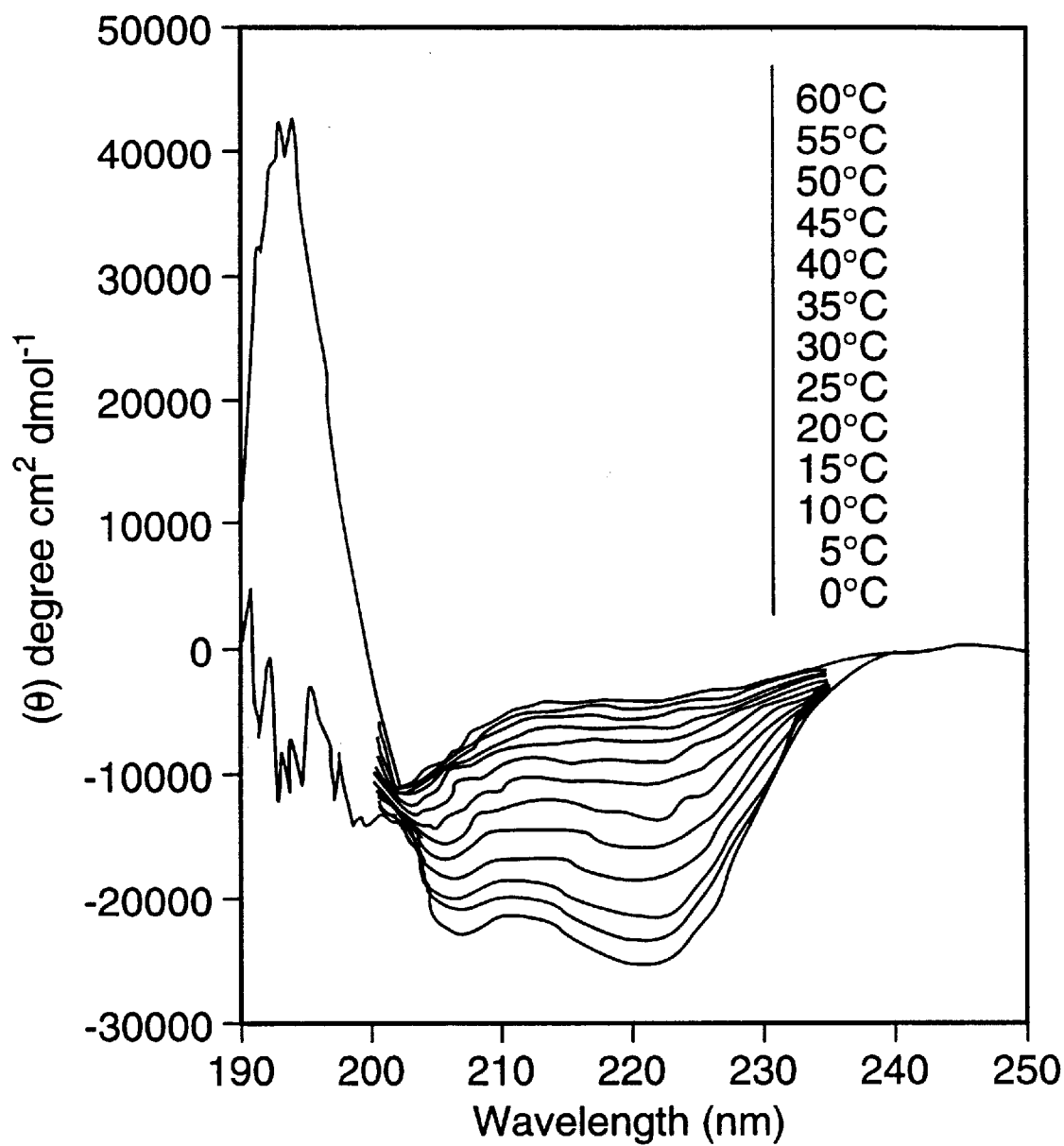
FIG. 12, panels A–C show CD spectra of liver and skin-specific AFPs at different temperatures.
Figure 12B:
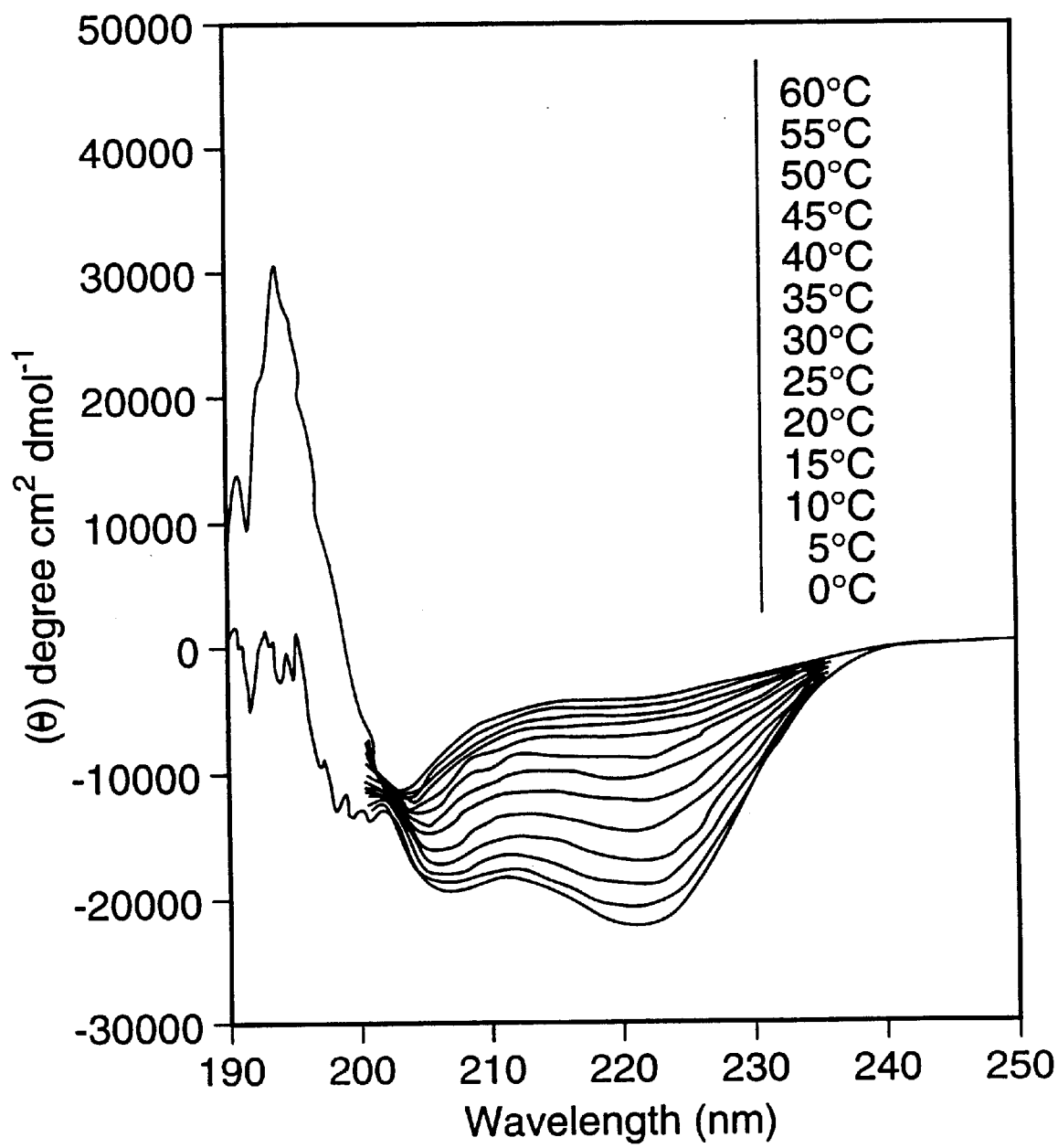
Figure 12C:
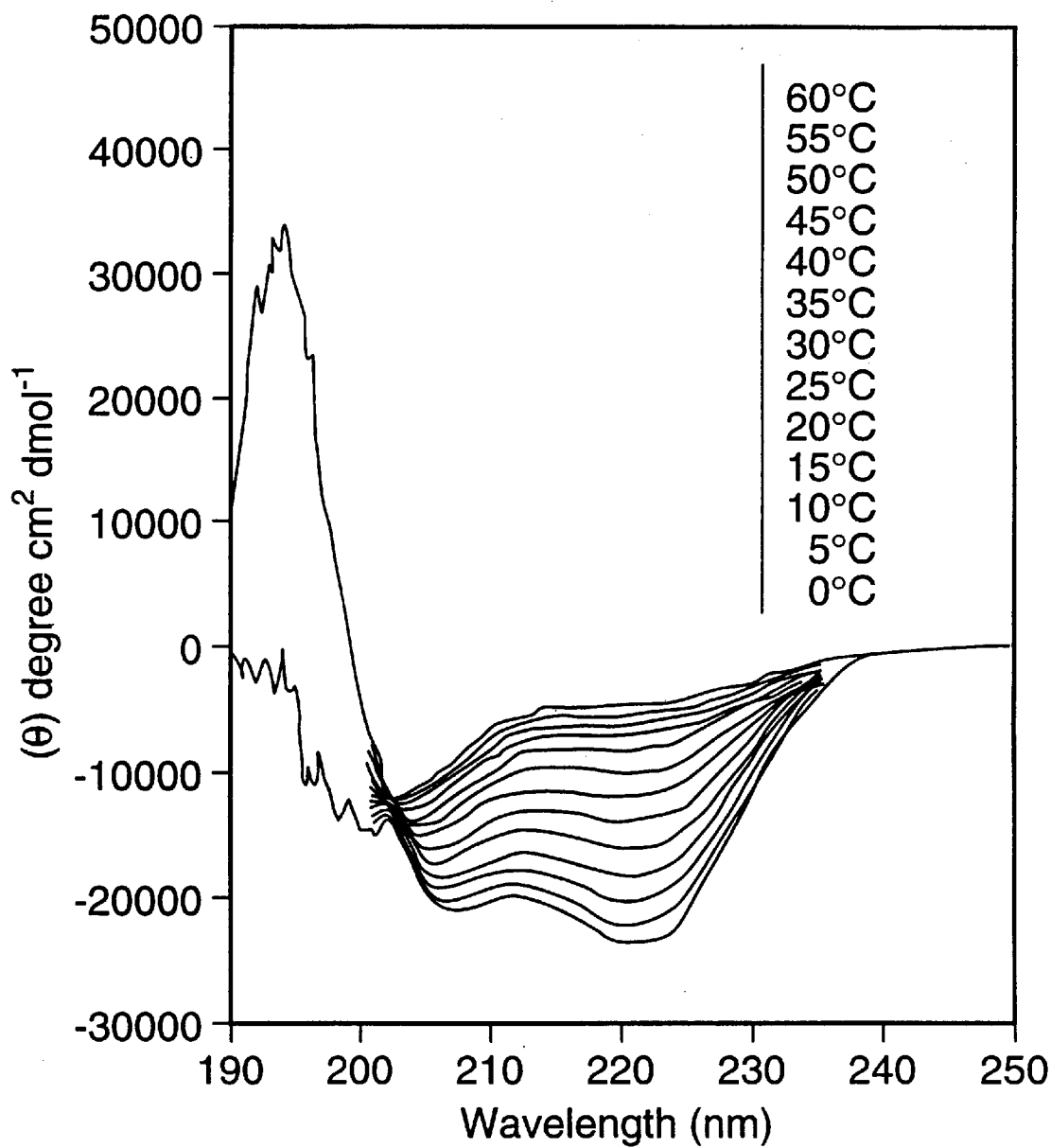

Thermal Stability of Skin Afps by Circular Dichroism and Thermal Denaturation Studies The secondary structure of both liver-type, extracellular AFPs (HPLC-6) and skin-type, intracellular AFPs (sAFP2, sAFP3) was determined by circular dichroism. Earlier studies showing that extracellular AFPs are helical at low temperatures were confirmed by x-ray crystallography (Ananthanarayan and Hew (1977) *Biochem. Biophys. Res. Comm.* 74, 685; Sicheri and Yang (1995) *Nature*, 375, 427–431). This example shows that the extracellular and intracellular AFPs are similar in their helical content (FIGS. 12, A–C and Table 1). At 0° C., sAFP2 and sAFP3 are 61 % and 67% helical as compared to 71% for HPLC-6. The helical content is much lower at higher temperatures; at 50° C., both types of AFPs are completely random coils. However, thermal denaturation is reversible in both cases (FIGS. 12, A–C).

CD spectra were measured using a Jasco J-600 spectropolarimeter. A water-jacketed (0.1 cm) quartz cell was used. Concentrations of peptides were calculated from UV-absorbance at 230 nm ($OD_{230}$=6.1 mM/L peptide-bonds). The concentrations of peptides for CD measurement were between 0.1–0.2 mg/ml in 0.1M $NH_4HCO_3$, pH 8.5. Thermal denaturation of the peptides were measured by varying temperatures from 0–60° C. with a 5° C. step gradient. After CD measurement at 60° C., the samples were cooled to 0° C. and the extent of refolding was determined. The mean residue ellipticity at a given wavelength $[q]_1$ was expressed in degree $cm^2$ $dmol^{-1}$. Fraction helix was calculated as described by Greenfield and Fasman (1969) *Biochemistry* 8, 4108–4116, employing 222 nm instead of 208 nm:

$$\text{Fraction helix} = \frac{[q]_{222}{}^{obs} - [q]_{222}{}^{coil}}{[q]_{222}{}^{helix} - [q]_{222}{}^{coil}}$$

The ellipticity $[q]_{222}{}^{coil}$ of each peptide in 6.0 M guanidine hydrochloride at 25° C. was assumed to represent 0% helix formation, and the ellipticity for $[q]_{222}{}^{helix}$ 100% helix formation was calculated from J. T. Yang et al. (1986) *Methods in Enzymology* 130, 208–269: $[q]^n = [q]^\infty (1-k/n)$; where n is the chain length and k is a wavelength-dependent factor (at 222 nm k=2.5 and $[q]\infty$=−37,400 degree $cm^2 dmol^{-1}$).

TABLE 1

THERMAL STABILITY OF LIVER AND SKIN AFPs

| AFP | Chain Length | $[\Theta]_{222}{}^a$ (deg $cm^2$ $dmol^{-1}$) | Fraction Helix | $Tm^b$ (° C.) |
|---|---|---|---|---|
| HPLC-6 | 37 | −25,240 | 0.71 | 15.8 |
| SAFP2 | 39 | −21,677 | 0.61 | 12.0 |
| SAFP3 | 39 | −23,577 | 0.67 | 15.8 |

[a]Measured at 0° C., pH 8.5, 0.1M $NH_4HCO_3$
[b]Temperature at which fraction helix is 0.5

Figure 13:
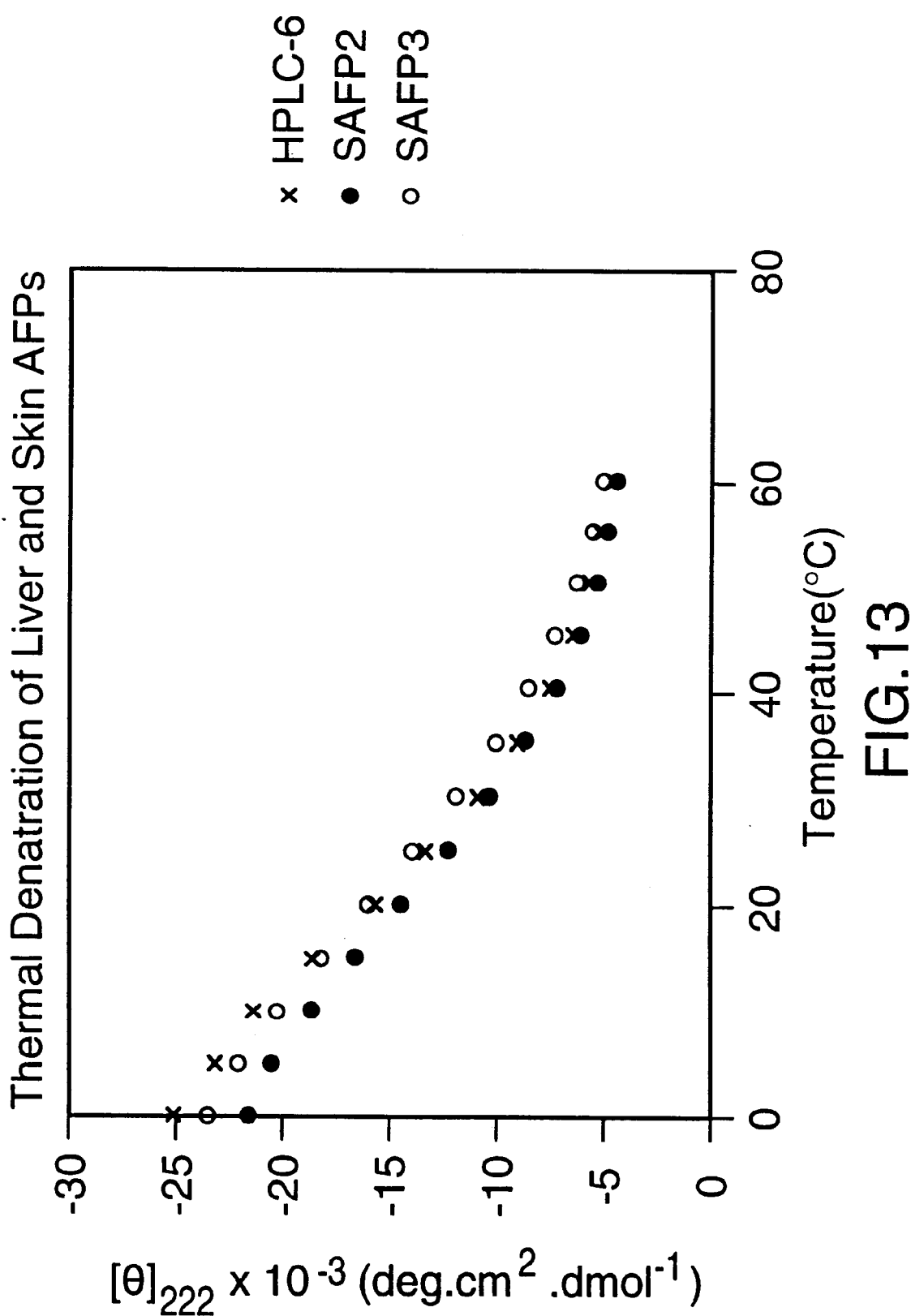
FIG. 13 shows a graph of the thermal denaturation of liver and skin-specific AFPs.

Thermal denaturation studies (FIG. 13) demonstrate that both types of flounder AFPs are similar in their Tm values. sAFP2 has a slightly lower rate at 12° C., as compared to 15.8° C. for both sAFP3 and HPLC-6 (Table 1).

Example 11

Ice Binding Motifs

Figure 14:
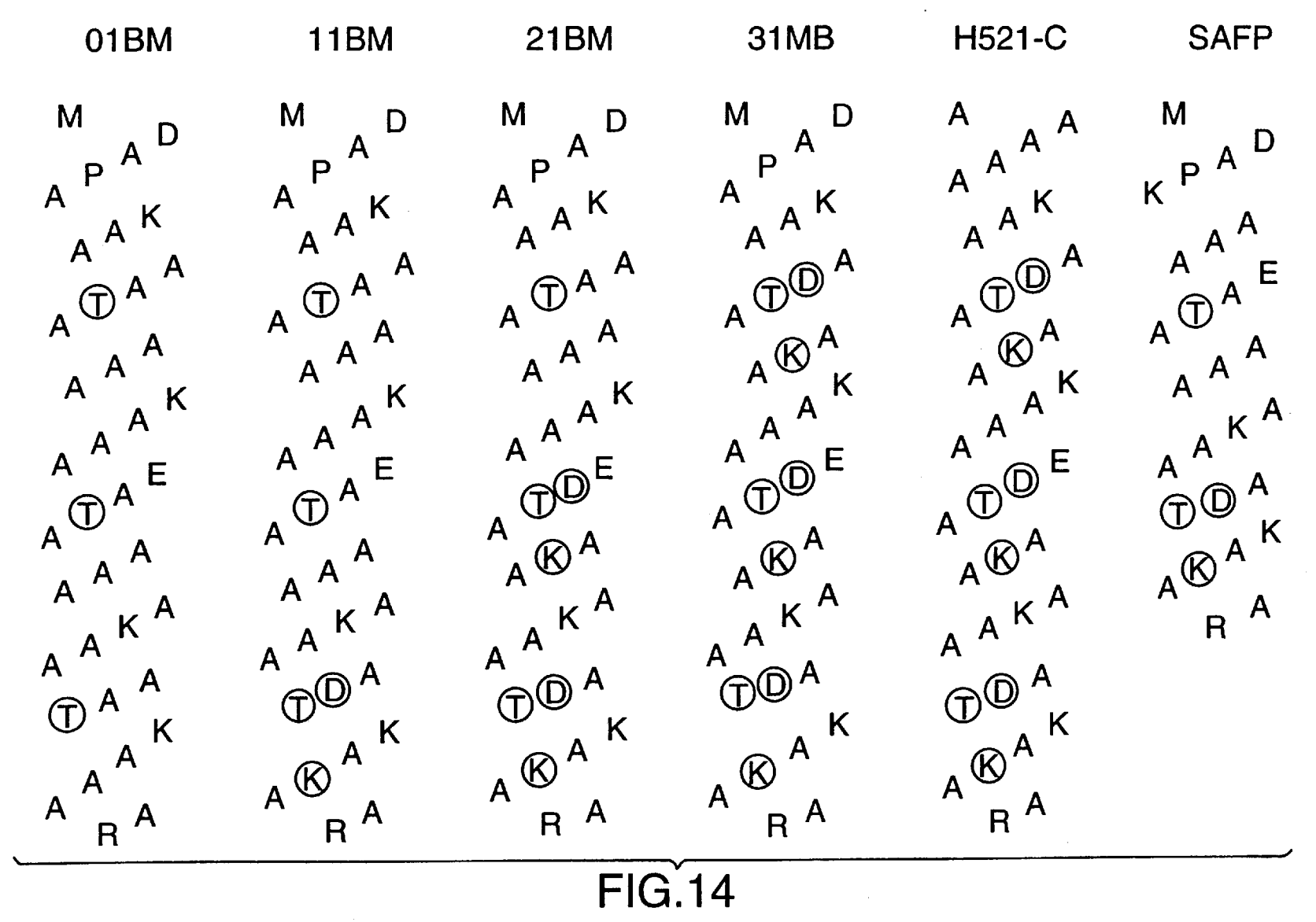
Figure 15:
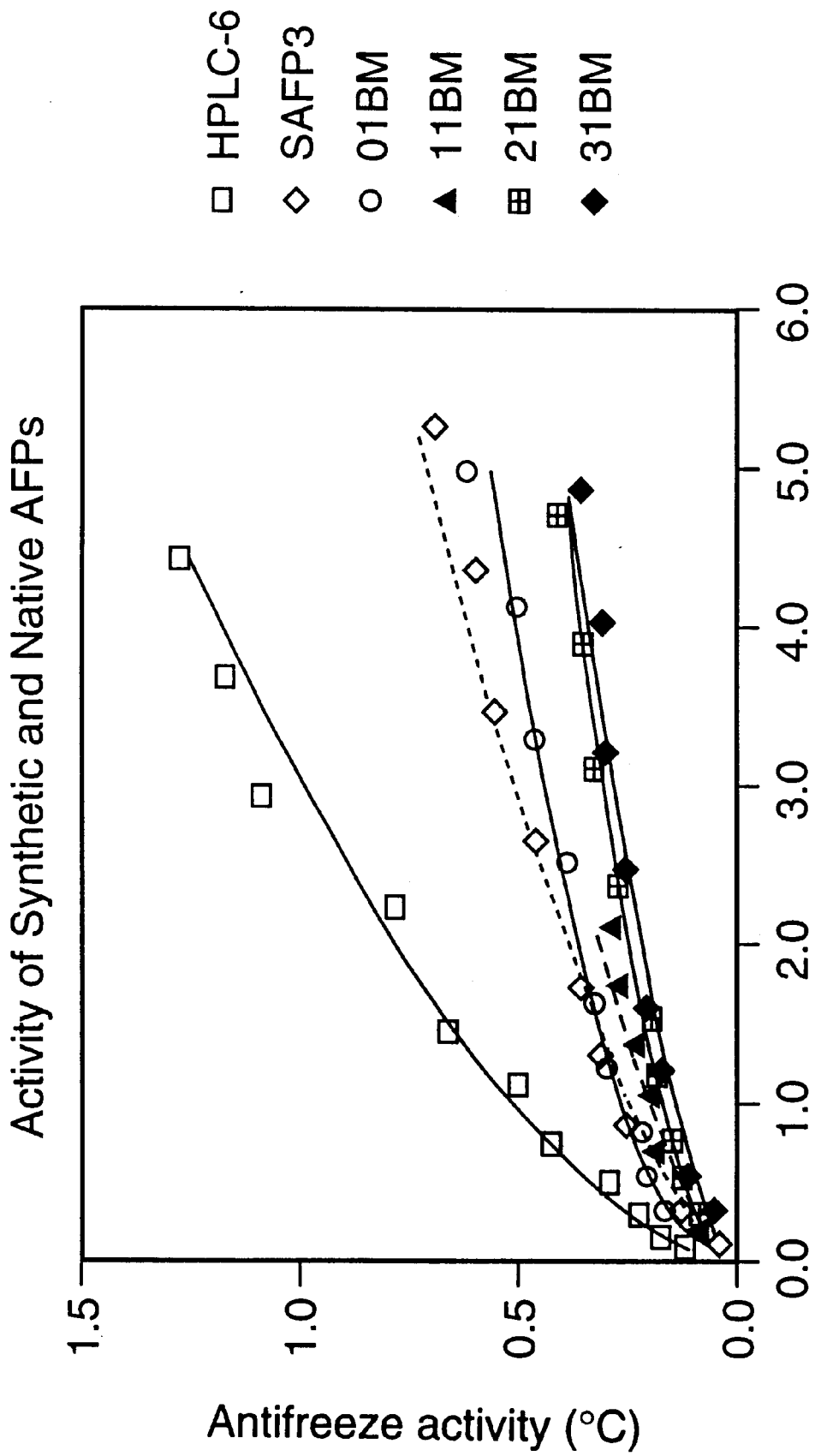
FIG. 15 shows the activity of synthetic and native AFPs.

Most of the intracellular AFPs lack the ice binding motifs (IBMs) that occur in the serum AFPs, such as "-LT—N-" or "-T—D-" in winter flounder or "-KT—D-" in sculpin AFPs, but instead contain only the Thr residues (incomplete IBMs) (see alxo, Sicheri and Yang (1995) *Nature*, 375, 427–431). However, one skin AFP, sAFP3, does contain a putative IBM, "-DT—K-". To compare this IBM with those of serum AFPs and to determine its role in ice binding in the skin AFPs, a series of synthetic peptides based on the structure of sAFP3 were prepared (Table 2). One peptide (1-IBM) was synthesized with the sequence of sAFP3, containing a single complete IBM. In other peptides, residues corresponding to the Asp and Lys of the complete IBM were substituted for Ala residues at specific positions in order to create new IBM motifs (FIG. 14; Table 2). A peptide containing no complete IBM (0-IBM) was synthesized by placing an Ala at the positions corresponding to the of the D and K of the IBM in the 1-IBM peptide. The activity of this peptide was slightly higher than that of the 1-IBM peptide, suggesting that loss of this IBM has no effect on antifreeze activity (FIG. 15). Peptide analogues containing 2 and 3 IBMs were slightly less active than the 1-IBM peptide. These peptides also appeared less helical as measured by CD.

A peptide analogue (521C) was prepared corresponding to the 3-IBM peptide but without the native N-terminal cap structure. This peptide showed approximately the same activity as the 3-IBM peptide. Note that the example modifications provided show that peptides similar to the native skin-type AFPs are made while retaining antifreeze activity.

TABLE 2

Amino Acid Sequence of Synthetic and Native
Skin Type Antifreeze Polypeptides

| | |
|---|---|
| 0IBM | MDAPAKAAAA TAAAAKAAAEA TAAAAAKAAAA TKAAAAR |
| 1IBM | MDAPAKAAAA TAAAAKAAAEA TAAAAAKAAAD TKAKAAR |
| 2IBM | MDAPAKAAAA TAAAAKAAAED TAAKAAKAAAD TKAKAAR |

TABLE 2-continued

Amino Acid Sequence of Synthetic and Native Skin Type Antifreeze Polypeptides

| | |
|---|---|
| 3IBM | MDAPAKAAAD TAAKAKAAAED TAAKAAKAAAD TKAKAAR |
| H521-C | AAAAAKAAAD TAAKAKAAAED TAAKAAKAAAD TKAKAAR |
| SAFP2 | MDAPAKAAAA TAAAAKAAAEA TAAAAAKAAAA TKAGAAR |
| SAFP3 | DAPAKAAAA TAAAAKAAAEA TAAAAAKAAAD TKAKAAR |

*01BM is SEQ ID NO: 35; 1IBM is SEQ ID NO: 36; 2IBM is SEQ ID NO: 37; 3IBM is SEQ ID NO: 38; H521-C is SEQ ID NO: 39; SAFP2 is SEQ ID NO: 18; SAFP3 is SEQ ID NO: 40.

Example 12

Peptide Synthesis

Peptides were synthesized at the Hospital for Sick Children Biotechnology Service Centre, Toronto, on the Pharmacia-LKB-Biolynx 4170 Automated Peptide Synthesizer (Pharmacia Biotech, Montreal, Quebec) using the continuous-flow Fmoc-chemistry on the NovaSyn KA 100 resin (Sheppard (1983) Chel??. Brit. 19:402–414). A solution of 20% piperidine in DMF was used for the removal of the Finoc-protection group. For each gram of resin (0.1 nmole substitution) four times excess of Fmoc-amino acid activated with diisopropylethylamine (1:1:2 mol/mol/mol) (Carpino et al.(1994) J. Chem. Soc. Chem. Commun. 201–203.Carpino et al., 1994) was used for the coupling reaction. The reaction time was 1 hr.

After the synthesis, the side-chain protected peptide-resin conjugates were acetylated separately using acetic anhydride/disopropylethylamine (2:1) at room temperature for 1 hr. The acetylated peptide-resin conjugates were washed with DMF, diethyl ether, and dried under reduced pressure. The dry peptide-resin conjugates were cleaved with 20 ml of TFA containing 4 ml thioanisole, 0.4 ml m-teresol, 2 ml 1,2-etanedithiol, 3 ml ethylmethylsufide and 4 ml bromotrimiiethylsulfide and 4 ml bromotrimethylsilane at 0° C. for 1 hr. The peptides were extracted, dissolved in 0.1% TFA and desalted on a Sephadex G10 column.

The homogeneity of the peptide was analyzed by reverse phase HPLC on a $\mu$Bondapak $C_{18}$ column, amino acid analysis and atmospheric pressure ionization mass spectrometry (API-MS (Carbohydrate Analysis Facility, University of Toronto).

All publications and patent applications cited in this specification are herein incorporated by reference as if each individual publication or patent application were specifically and individually indicated to be incorporated by reference in its entirety for all purposes. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated skin-type intracellular antifreeze polypeptide, wherein the polypeptide comprises an N terminal Met-Asp-Ala-Pro (SEQ ID NO:1) subsequence;

the polypeptide comprises an internal Ala-Ala-Thr-Ala-Ala-Ala-Ala-Lys-Ala-Ala-Ala (SEQ ID NO:2) subsequence;

the polypeptide does not comprise a signal sequence;

the polypeptide induces a concentration-dependent decrease in the freezing point of an aqueous solution; and, conservative modifications thereof.

2. The isolated polypeptide of claim 1, wherein the polypeptide has a molecular of about 3400 Da.

3. The isolated polypeptide of claim 1, wherein the polypeptide has an N terminal Met-Asp-Ala-Pro-Ala (SEQ ID NO:9) sequence.

4. The isolated polypeptide of claim 1, wherein the polypeptide is from about 35 to about 55 amino acids in length.

5. The isolated polypeptide of claim 1, wherein the polypeptide comprises the sequence Met-Asp-Ala-Pro-Ala-$X_1$-Ala-Ala-Ala-Ala-Thr-Ala-Ala-Ala-Ala-Lys-Ala-Ala-Ala-Glu-Ala-Thr-$X_2$-Ala-Ala-Ala-Ala-$X_2$-Ala-Ala-Ala-$X_3$-Thr (SEQ ID NO:3); wherein, $X_1$ is selected from the group consisting of Arg, Lys, and Ala;

$X_2$ is selected from the group consisting of Lys and Ala; and, $X_3$ is selected from the group consisting of Ala and Asp and a bond.

6. The isolated polypeptide of claim 1, wherein the polypeptide is selected from the group consisting of sAFP1 (SEQ ID NO:16), sAFP2 (SEQ ID NO:18), sAFP3 (SEQ ID NO:20), sAFP4 (SEQ ID NO:22), sAFP5 (SEQ ID NO:24), sAFP6 (SEQ ID NO:26), sAFP7 (SEQ ID NO:28), sAFP8 (SEQ ID NO:30), and 11-3 (SEQ ID NO:32).

7. The isolated polypeptide of claim 1, wherein the polypeptide binds t pool of subtracted polyclonal antibodies, wherein the subtracted polyclonal antibodies are raised against the sAFP1 (SEQ ID NO:16) polypeptide and subtracted within HPLC-6 polypeptide (SEQ ID NO:39).

8. The isolated polypeptide of claim 1, wherein the isolated polypeptide is a component of an aqueous solution.

9. The isolated polypeptide of claim 1, wherein the polypeptide is from about 60% to about 70% helical as measured by circular dichroism.

10. The isolated polypeptide of claim 1, wherein the polypeptide is a fusion protein.

11. The isolated skin-type intracellular antifreeze polypeptide of claim 1, which is encoded by a nucleic acid molecule, which nucleic acid molecule hybridizes to a skin type antifreeze nucleic acid molecule selected from the group consisting of sAFP1 (SEQ ID NO:15), sAFP2 (SEQ ID NO:17), sAFP3 (SEQ ID NO:19), sAFP4 (SEQ ID NO:21), sAFP5 (SEQ ID NO:23), sAFP6 (SEQ ID NO:25), sAFP7 (SEQ ID NO:27), sAFP8 (SEQ ID NO:29), F2 (SEQ ID NO:33) and 11-3 (SEQ ID NO:31) in a northern blot under high stringency wash conditions of 0.015M NaCl at 72° C., wherein the nucleic acid molecule does not hybridize to SEQ ID NO:41 under high stringency wash conditions of 0.015NaCl at 72° C.

12. The isolated polypeptide of claim 11, wherein the polypeptide is selected from the group consisting of sAFP1 (SEQ ID NO:16), sAFP2 (SEQ ID NO:18), sAFP3 (SEQ ID NO:20), sAFP4 (SEQ ID NO:22), sAFP5 (SEQ ID NO:24), sAFP6 (SEQ ID NO:26), sAFP7 (SEQ ID NO:28), sAFP8 (SEQ ID NO:30), and 11-3 (SEQ ID NO:32).

13. A method of making an aqueous composition resistant to freezing, comprising adding a skin-type antifreeze polypeptide to the composition in an amount sufficient to change the thermal hysteresis of the composition, wherein the skin-type antifreeze polypeptide comprises an N terminal Met-Asp-Ala-Pro (SEQ ID NO:1) subsequence, and an internal Ala-Ala-Thr-Ala-Ala-Ala-Ala-Lys-Ala-Ala-Ala (SEQ ID NO:2) subsequence; and wherein the polypeptide does not comprise a signal sequence.

14. The method of claim 13, wherein the step of adding the skin type antifreeze peptide is performed in a cell, wherein the skin type antifreeze polypeptide is added to the cell by transforming the cell with a nucleic acid which encodes the skin type antifreeze polypeptide and expressing the antifreeze polypeptide in the cell.

* * * * *

UNITED STATES PATENT AND TRADEMARK OFFICE
CERTIFICATE OF CORRECTION

PATENT NO.    : 6,307,020 B1                                                    Page 1 of 1
DATED         : October 23, 2001
INVENTOR(S)   : Choy Hew et al.

It is certified that error appears in the above-identified patent and that said Letters Patent is hereby corrected as shown below:

Column 65,
Line 32, after "molecular" insert -- weight --.
Line 57, delete "t" and insert therefor -- to a --.

Column 66,
Line 36, delete "0.015NaCl" and insert therefor -- 0.015M NaCl --.

Signed and Sealed this

Twenty-fifth Day of March, 2003

JAMES E. ROGAN
*Director of the United States Patent and Trademark Office*

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:

Met Asp Ala Pro
1

(2) INFORMATION FOR SEQ ID NO:2:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

Ala Ala Thr Ala Ala Ala Ala Lys Ala Ala Ala
1            5                  10

(2) INFORMATION FOR SEQ ID NO:3:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER" /note= "Xaa = Arg,
            Lys or Ala"

(ix) FEATURE:
        (A) NAME/KEY: Modified-site
        (B) LOCATION: 23
        (D) OTHER INFORMATION: /product= "OTHER" /note= "Xaa = Lys or
            Ala"

(ix) FEATURE:
        (A) NAME/KEY: Modified-site
        (B) LOCATION: 28
        (D) OTHER INFORMATION: /product= "OTHER" /note= "Xaa = Lys or
            Ala"

(ix) FEATURE:
        (A) NAME/KEY: Modified-site
        (B) LOCATION: 32
        (D) OTHER INFORMATION: /product= "OTHER" /note= "Xaa = Ala,
            Asp or none"

(xi) SEQUENCE DESCRIPTION: SEQ ID NO:3:

```
Met Asp Ala Pro Ala Xaa Ala Ala Ala Ala Thr Ala Ala Ala Ala Lys
1               5                   10                  15

Ala Ala Ala Glu Ala Thr Xaa Ala Ala Ala Ala Xaa Ala Ala Ala Xaa
            20                  25                  30

Thr
```

(2) INFORMATION FOR SEQ ID NO:4:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CATCAGGACT CAAACACTTT TCACTGTCGA CCACTCAG                    38

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Thr Xaa Xaa Xaa Xaa Xaa Xaa Xaa
1               5
```

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Thr Xaa Xaa Asx Xaa Xaa Xaa Xaa Xaa
1               5

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

CTCAGAATCA CTGACATCAA AATGGACGCA CCAGCC                                  36

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GGCTGGTGCG TCCATTTTGA TGTCAGTGAT TCTGAG                                  36

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Met Asp Ala Pro Ala
1               5

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GGCTGGTGCG TCCATGTTGA TG                                                 22

(2) INFORMATION FOR SEQ ID NO:11:

(i) SEQUENCE CHARACTERISTICS:
        (A) LENGTH: 24 base pairs (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:11:

CATATGGACG CACCAGCCAA AGCC                                              24

(2) INFORMATION FOR SEQ ID NO:12:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:12:

GGATCCTTAA CGGGCTGCTC CGGC                                              24

(2) INFORMATION FOR SEQ ID NO:13:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:13:

GCGGCCGCAT GGACGCACCA GCCAAAGCC                                         29

(2) INFORMATION FOR SEQ ID NO:14:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

GCGGCCGCTT AACGGGCTGC TCCGGC                                            26

(2) INFORMATION FOR SEQ ID NO:15:

(i) SEQUENCE CHARACTERISTICS:
            (A) LENGTH: 241 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 33..149
            (D) OTHER INFORMATION: /product= "sAFP1 (S4)" /note=
                "skin-type antifreeze polypeptide 1 (sAFP1)"

(xi) SEQUENCE DESCRIPTION: SEQ ID NO:15:

ACTGTCGACC ACTCAGAATC ACTGACATCA AC ATG GAC GCA CCA GCC AGA GCC         53
                                    Met Asp Ala Pro Ala Arg Ala
                                     1               5

GCC GCA GCC ACC GCC GCC GCC GCC AAG GCC GCC GCA GAA GCC ACC AAA        101

```
Ala Ala Ala Thr Ala Ala Ala Ala Lys Ala Ala Glu Ala Thr Lys
        10              15                  20

GCC GCA GCC GCC AAA GCA GCA GCT GCC ACC AAA GCC GCA GCC CAT      146
Ala Ala Ala Ala Lys Ala Ala Ala Ala Thr Lys Ala Ala Ala His
    25                  30                  35

TAATGATCGT GGTCGTCTTG ATGTGGGATC ATGTGAACAT CTGAGCAGCG AGATGTTACC    206

AATCTGCTGA ATAAACCTGA GAAGCTGTTT GTTGA                              241

(2) INFORMATION FOR SEQ ID NO:16:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:16:

Met Asp Ala Pro Ala Arg Ala Ala Ala Thr Ala Ala Ala Ala Lys
 1           5                  10                  15

Ala Ala Ala Glu Ala Thr Lys Ala Ala Ala Ala Lys Ala Ala Ala Ala
            20                  25                  30

Thr Lys Ala Ala Ala His
        35

(2) INFORMATION FOR SEQ ID NO:17:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 37..156
        (D) OTHER INFORMATION: /product= "sAFP2 (S3)" /note=
            "skin-type antifreeze polypeptide 2 (sAFP2)"

(xi) SEQUENCE DESCRIPTION: SEQ ID NO:17:

TTTCACTGTC GACCACTCAG AATCACTGAC ATCAAC ATG GAC GCA CCA GCC AAA      54
                                        Met Asp Ala Pro Ala Lys
                                         1               5

GCC GCC GCA GCC ACC GCC GCC GCC GCC AAG GCC GCC GCA GAA GCC ACC    102
Ala Ala Ala Ala Thr Ala Ala Ala Ala Lys Ala Ala Ala Glu Ala Thr
        10                  15                  20

GCC GCC GCA GCT GCC AAA GCA GCA GCC GCC ACC AAA GCC GGA GCA GCC    150
Ala Ala Ala Ala Ala Lys Ala Ala Ala Ala Thr Lys Ala Gly Ala Ala
    25                  30                  35

CGT TAATGATCGT GGTCGTCTTG ATGTGGGATC ATGTGAACAT CTGAGCAGCG          203
Arg

AGATGTTACC AATCTGCTGA ATAAACCTGA GAAGCTGTTT GTTGA                  248

(2) INFORMATION FOR SEQ ID NO:18:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:18:
```

```
Met Asp Ala Pro Ala Lys Ala Ala Ala Thr Ala Ala Ala Ala Lys
  1               5                  10                  15

Ala Ala Ala Glu Ala Thr Ala Ala Ala Lys Ala Ala Ala Ala
                 20                  25                  30

Thr Lys Ala Gly Ala Ala Arg
         35
```

(2) INFORMATION FOR SEQ ID NO:19:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 30..149
        (D) OTHER INFORMATION: /product= "sAFP3 (P9)" /note=
           "skin-type antifreeze polypeptide 3 (sAFP3)"

(xi) SEQUENCE DESCRIPTION: SEQ ID NO:19:

```
GTCGAACACT CAGAATCACT GACATCAAC ATG GAC GCA CCA GCC AAA GCC GCC         53
                                Met Asp Ala Pro Ala Lys Ala Ala
                                 1               5

GCA GCC ACC GCC GCC GCC GCC AAG GCC GCC GCA GAA GCC ACC GCC GCC        101
Ala Ala Thr Ala Ala Ala Ala Lys Ala Ala Ala Glu Ala Thr Ala Ala
         10                  15                  20

GCA GCC GCC AAA GCA GCA GCC GAC ACC AAA GCC AAA GCA GCC CGT            146
Ala Ala Ala Lys Ala Ala Ala Asp Thr Lys Ala Lys Ala Ala Arg
 25                  30                  35

TAAGGATCGT GGTCGTCTTG ATGTGGGATC ATGTGAACAT CTGAGCAGCG AGATGTTACC       206

AATCTGCTGA ATAAACCTGA GAAGCTGTTT TTTA                                   240
```

(2) INFORMATION FOR SEQ ID NO:20:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:20:

```
Met Asp Ala Pro Ala Lys Ala Ala Ala Thr Ala Ala Ala Ala Lys
  1               5                  10                  15

Ala Ala Ala Glu Ala Thr Ala Ala Ala Lys Ala Ala Ala Asp
                 20                  25                  30

Thr Lys Ala Lys Ala Ala Arg
         35
```

(2) INFORMATION FOR SEQ ID NO:21:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS (B) LOCATION: 30..149
        (D) OTHER INFORMATION: /product= "sAFP4 (P7)" /note=
            "skin-type antifreeze polypeptide 4 (sAFP4)"

(xi) SEQUENCE DESCRIPTION: SEQ ID NO:21:

```
GTCGACCACT CAGAATCACT GACATCAAC ATG GAC GCA CCA GCC AAA GCC GCC        53
                                Met Asp Ala Pro Ala Lys Ala Ala
                                  1               5

GCA GCC ACC GCC GCC GCC GCC AAG GCC GCC GCA GAA GCC ACC GCC GCC       101
Ala Ala Thr Ala Ala Ala Ala Lys Ala Ala Ala Glu Ala Thr Ala Ala
         10                  15                  20

GCA GCT GCC AAA GCA GCA GCC GCC ACC AAA GCC GGA GCA GCC CAT           146
Ala Ala Ala Lys Ala Ala Ala Ala Thr Lys Ala Gly Ala Ala His
 25                  30                  35

TAATGATCGT GGTCGTCTTG ATGTGGGATC ATGTGAACAT CTGAGCAGCG AGATGTTACC     206

AATCTGCTGA ATAAACCTGA AAGCTGTTT GTTGAAAAAA AAAAAAAAAA AAAAAA          262
```

(2) INFORMATION FOR SEQ ID NO:22:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:22:

```
Met Asp Ala Pro Ala Lys Ala Ala Ala Thr Ala Ala Ala Ala Lys
  1               5                  10                  15

Ala Ala Ala Glu Ala Thr Ala Ala Ala Ala Lys Ala Ala Ala Ala
                 20                  25                  30

Thr Lys Ala Gly Ala Ala His
                 35
```

(2) INFORMATION FOR SEQ ID NO:23:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 39..155
        (D) OTHER INFORMATION: /product= "sAFP5 (S2)" /note=
            "skin-type antifreeze polypeptide 5 (sAFP5)"

(xi) SEQUENCE DESCRIPTION: SEQ ID NO:23:

```
CTTTTCACTG TCGACCACTC AGAATCACTG ACATCAAC ATG GAC GCA CCA GCC          53
                                          Met Asp Ala Pro Ala
                                            1               5

AAA GCC GCC GCA GCC ACC GCC GCC GCC GCC AAG GCC GCC GCA GAA GCC       101
Lys Ala Ala Ala Ala Thr Ala Ala Ala Ala Lys Ala Ala Ala Glu Ala
             10                  15                  20

ACC AAA GCC GCA GCC GCC AAA GCA GCA GCT GCC ACC AAA GCC GCA GCC       149
Thr Lys Ala Ala Ala Ala Lys Ala Ala Ala Ala Thr Lys Ala Ala Ala
                 25                  30                  35

CAT TAATGATCGT GGTCGTCTTG CTGTGGGATC ATGTGAACAT CTGAGCAGCG             202
His

AGATGTTACC AATCTGCTGA ATAAACCTGA AAGCTGTTT GTTGA                      247
```

(2) INFORMATION FOR SEQ ID NO:24:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:24:

Met Asp Ala Pro Ala Lys Ala Ala Ala Ala Thr Ala Ala Ala Lys
 1               5                  10                  15

Ala Ala Ala Glu Ala Thr Lys Ala Ala Ala Lys Ala Ala Ala Ala
            20                  25                  30

Thr Lys Ala Ala Ala His
        35

(2) INFORMATION FOR SEQ ID NO:25:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 20..136
        (D) OTHER INFORMATION: /product= "sAFP6 (L4)" /note=
            "skin-type antifreeze polypeptide 6 (sAFP6)"

(xi) SEQUENCE DESCRIPTION: SEQ ID NO:25:

```
CAGAATCACT GACATCAAC ATG GAC GCA CCA GCC AAA GCC GCC GCA GCC ACC      52
                    Met Asp Ala Pro Ala Lys Ala Ala Ala Ala Thr
                     1               5                      10

GCC GCC GCC GCC AAG GCC GCC GCA GAA GCC ACC GCC GCC GCA GCT GCC     100
Ala Ala Ala Ala Lys Ala Ala Ala Glu Ala Thr Ala Ala Ala Ala Ala
            15                  20                  25

AAA GCA GCC GCC ACC AAA GCC GGA GCA GCC CGT TAATGATCGT GGTCGTCTTG    153
Lys Ala Ala Ala Thr Lys Ala Gly Ala Ala Arg
            30                  35

ATGTGGGATC ATGTGAACAT CTGAGCAGCG AGATGTTACC AATCTGCTGA ATAAACCTGA    213

GAAGCTGTTT GTTGA                                                     228
```

(2) INFORMATION FOR SEQ ID NO:26:

(i) SEQUENCE CHARACTERISTICS:
        (A) LENGTH: 38 amino acids
        (B) TYPE: amino acid
        (D) TOPOLOGY: linear (ii) MOLECULE TYPE: protein (xi) SEQUENCE DESCRIPTION: SEQ ID NO:26:

Met Asp Ala Pro Ala Lys Ala Ala Ala Thr Ala Ala Ala Ala Lys
 1               5                  10                  15

Ala Ala Ala Glu Ala Thr Ala Ala Ala Ala Lys Ala Ala Ala Thr
            20                  25                  30

Lys Ala Gly Ala Ala Arg
        35

(2) INFORMATION FOR SEQ ID NO:27:

(i) SEQUENCE CHARACTERISTICS:
    (A) LENGTH: 245 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 34..153
    (D) OTHER INFORMATION: /product= "sAFP7 (S9)" /note=
        "skin-type antifreeze polypeptide 7 (sAFP7)"

(xi) SEQUENCE DESCRIPTION: SEQ ID NO:27:

```
CACTGTCGAC CACTCAGAAT CACTGACATC AAC ATG GAC GCA CCA GCC GCC GCC        54
                                    Met Asp Ala Pro Ala Ala Ala
                                     1               5

GCC GCA GCC ACA GCC GCC GCC GCC AAG GCC GCC GCC GAA GCC ACC GCA       102
Ala Ala Ala Thr Ala Ala Ala Ala Lys Ala Ala Ala Glu Ala Thr Ala
         10                  15                  20

GCT GCC GCA GCC AAA GCA GCA GCC GCC ACC AAA GCC GCA GCA GCC CGT       150
Ala Ala Ala Ala Lys Ala Ala Ala Ala Thr Lys Ala Ala Ala Ala Arg
     25                  30                  35

TAAGGATCGT GGTCGTCTTG CTGTGGGATC ATGTGAACAT CTGAGCAGCG AGATGTTACC     210

AATCTGCTGA ATAAACCTGA GAAGCTGTTT GTTTA                                245
```

(2) INFORMATION FOR SEQ ID NO:28:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:28:

```
Met Asp Ala Pro Ala Ala Ala Ala Ala Thr Ala Ala Ala Ala Lys
 1               5                  10                  15

Ala Ala Ala Glu Ala Thr Ala Ala Ala Ala Lys Ala Ala Ala Ala
             20                  25                  30

Thr Lys Ala Ala Ala Ala Arg
         35
```

(2) INFORMATION FOR SEQ ID NO:29:

(i) SEQUENCE CHARACTERISTICS:
        (A) LENGTH: 292 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 36..200
        (D) OTHER INFORMATION: /product= "sAFP8 (S6)" /note=
            "skin-type antifreeze polypeptide 8 (sAFP8)"

(xi) SEQUENCE DESCRIPTION: SEQ ID NO:29:

```
TTCACTGTCG AACACTCAGA ATCACTGACA TCAAC ATG GAC GCA CCA GCC GCC       53
                                       Met Asp Ala Pro Ala Ala
                                        1               5

GCC GCC GCA GCC ACC GCC GCC GCC GCC AAG GCC GCC GCA GAA GCC ACC      101
Ala Ala Ala Ala Thr Ala Ala Ala Ala Lys Ala Ala Ala Glu Ala Thr
```

|  |  |  | 10 |  |  | 15 |  |  | 20 |  |  |  |  |  |
|--|--|--|--|--|--|--|--|--|--|--|--|--|--|--|
| GCA | GCT | GCC | GCA | GCC | GCA | GCC | GCC | GCA | GCC | ACT | GCC | GAA | GCC | GCC | GCC | 149 |
| Ala | Ala | Ala | Ala | Ala | Ala | Ala | Ala | Ala | Ala | Thr | Ala | Glu | Ala | Ala | Ala |  |
|  |  |  | 25 |  |  |  | 30 |  |  |  | 35 |  |  |  |  |  |

| AAA | GCA | GCC | GCC | GCC | ACC | AAA | GCC | GCA | GCC | GCC | GCA | GCC | GCC | GCC | CGT | 197 |
|--|--|--|--|--|--|--|--|--|--|--|--|--|--|--|--|--|
| Lys | Ala | Ala | Ala | Ala | Thr | Lys | Ala | Ala | Ala | Ala | Ala | Ala | Ala | Ala | Arg |  |
|  | 40 |  |  |  |  | 45 |  |  |  |  | 50 |  |  |  |  |  |

```
TAAGGATCAT CGTCGTCTTG CTGTGGGATC ATGTGAACAT CTGAGCAGCG AGATGTCACC     257

AATCTGTTGA ATAAAGCTGA GAAGCTGTTT GTTTA                                292
```

(2) INFORMATION FOR SEQ ID NO:30:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO:30:

| Met | Asp | Ala | Pro | Ala | Ala | Ala | Ala | Ala | Thr | Ala | Ala | Ala | Ala | Lys |
|--|--|--|--|--|--|--|--|--|--|--|--|--|--|--|
| 1 |  |  |  | 5 |  |  |  |  | 10 |  |  |  |  | 15 |

| Ala | Ala | Ala | Glu | Ala | Thr | Ala | Ala | Ala | Ala | Ala | Ala | Ala | Ala |
|--|--|--|--|--|--|--|--|--|--|--|--|--|--|
|  |  |  | 20 |  |  |  |  | 25 |  |  |  |  | 30 |

| Thr | Ala | Glu | Ala | Ala | Ala | Lys | Ala | Ala | Ala | Ala | Thr | Lys | Ala | Ala | Ala |
|--|--|--|--|--|--|--|--|--|--|--|--|--|--|--|--|
|  | 35 |  |  |  |  | 40 |  |  |  |  | 45 |  |  |  |  |

| Ala | Ala | Ala | Ala | Ala | Arg |
|--|--|--|--|--|--|
|  | 50 |  |  |  |  |

(2) INFORMATION FOR SEQ ID NO:31:

(i) SEQUENCE CHARACTERISTICS:
        (A) LENGTH: 1287 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 973..1092
        (D) OTHER INFORMATION: /product= "11-3" /note=
           "antifreeze polypeptide 11-3"

(xi) SEQUENCE DESCRIPTION: SEQ ID NO:31:

```
TTACAAAACA AGTTCATACT GGATGGTTGC CACACCTTCC TGTTGATGTG AACCAGTCGG     60

AGCCGACGCC CTGCTGCGTC ACGAAATCAA AGTGAATAAA TAGAGGCTGC TCCCTAAAAG    120

TTTTCATCAG GACTCAAACA CTTTTCACTG TCGACCACTC AGGTACGTGA ACACTCACTT    180

TGTTTCTCAT ACAAATCTGG TTTTACTGTA AATATCTTGG GAAGGAAGGA AGGATATCTG    240

CATTATCCTG AGGGGCCATT TGTTTTACAG CCAGCGGTGA AGATGAAGA TCTTCATCCA     300

TGTTCGTCTG ATGGAAAGTT TGTTCTGAAA CCTTCAGTGG AAGAAACAGA TTCATGTCTT    360

CAGGCTTAAA CCTGCAAAAA TCTGAGCTCT GTTAAATCAT GGGAAACAAC TTTTTAATTC    420

AGTCAGGGCT GGAAAACTAT TTTATATGCA CAGAAGAAGA AGAAGTGATC TTTAGTTCAT    480

CACCATGGAA ACATCATCAG CAGTTAAAGT CTGTCTGCTT CAGTATCACC GGCCAGTTCC    540

AGTGCTCATG TTTCTGATCA GCTTGGTTTG AATGATATAA AAACGGATTG AGTGCCTGTT    600

TGACCCTGTT TAACACAAGA TTGGACGCAT GGACCATCTT TATTTACATA ATGTTTTACA    660
```

```
TCAGCACTTC CTGTTTTCAG CCCTAAACTT AAAGAGGCCT CATGGAAACT TCCTGATGAT      720

CTGGTGACAC CTGCTGGTTG AAGGAAACAG AGTTTGAGAG GCAGCAGAAA AAATGATTTT      780

AGTTTGAATG AAGAAGCTGT CATTTTATTT TATATTTGGA GGGGGGGGGG GGGGGATCAC      840

CACACACAGA TATTGAACAC TGTCATCACT GGGTTCGGTG AAAGTGAAGA ACCAGTACAT      900

GTTGTGATAT ATAATATTAT CATAATAATT ATAATTAATA CCATTAATCT CTGCAGAATC      960

ACTGACATCA AC ATG GAC GCA CCA GCC AAA GCC GCC GCA GCC ACC GCC         1008
              Met Asp Ala Pro Ala Lys Ala Ala Ala Ala Thr Ala
                1              5                  10

GCC GCC GCC AAG GCC GCC GCA GAA GCC ACC GCC GCC GCA GCT GCC AAA       1056
Ala Ala Ala Lys Ala Ala Ala Glu Ala Thr Ala Ala Ala Ala Ala Lys
             15                  20                  25

GCA GCA GCC GCC ACC AAA GCC GCA GCA GCC CGT TAATGATCGT GGTCGTCTTG     1109
Ala Ala Ala Ala Thr Lys Ala Ala Ala Ala Arg
         30                  35

ATGTGGGATC ATGTGAACAT CTGAGCAGCG AGATGTTACC AATCTGCTGA ATAAACCTGA     1169

GAAGCTGTTT GTTTAAAACC AAGTGTCCTG TTCATTTCAT CTCTGAAACT CATTCACAGT     1229

TTCTGTAGAT CATGTTTTTA TTTTGTTCAG ACGATGTTGA ACTGGATCAG AATCCAGA       1287

(2) INFORMATION FOR SEQ ID NO:32:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO:32:

Met Asp Ala Pro Ala Lys Ala Ala Ala Ala Thr Ala Ala Ala Ala Lys
  1               5                  10                  15

Ala Ala Ala Glu Ala Thr Ala Ala Ala Ala Lys Ala Ala Ala Ala
             20                  25                  30

Thr Lys Ala Ala Ala Ala Arg
         35

(2) INFORMATION FOR SEQ ID NO:33:

(i) SEQUENCE CHARACTERISTICS:
        (A) LENGTH: 1236 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..1236
        (D) OTHER INFORMATION: /label= F2

(ix) FEATURE:
        (A) NAME/KEY: CDS
        (B) LOCATION: 22..1041
        (D) OTHER INFORMATION: /product= "sAFP2" /note=
            "skin-type antifreeze polypeptide 2 (sAFP2)"

(xi) SEQUENCE DESCRIPTION: SEQ ID NO:33:

TTACAAAACA AGTTCATACT GGCCTGGATG GTCGCCACAC CTTCCTGTTG ATGTGAACCA       60

GTCGGAGCCG ACGCCCTGCT GCGTCACAAA ATCAAAGTGA ATAAATAGAG GCTGCTCCCT      120

AAAAGTTTTC ATCAGGACTC AAACACTTTT CACTGTCGAC CACTCAGGTA CGTGAACACT      180
```

-continued

```
CACTTTGTTT CTCTTACAAA TTTGTTTTAC TGTAAATATC TTGGGAAGGA AGGAAGGATA      240

TCTGCATTAT CCGAGGGGCC ATTTGTTTTA CAGCCAGCGG TGAAAGATGA AGATCTTCAT      300

CCGTGTTCGT ATGATGGAAA GTTTGTTCTG AAACCTTCAT TGGAAGAAAC AGATTCATGT      360

GTTCAGGCTT AAACCTGCAA AAATCTGAGC TCTGTTAAAT CATGGGAAAC AACTTTATAA      420

TTCAGTCAGG GCTGGAAAAC TCTTTTATAT GCACAGAAGA AGAAGAAGAT GTGATCTTTA      480

GTTCATCACC ATGGAAACAT CATCAGCAGT TAAAGTCTGT CTGCTTCAGT ATCACCGGCC      540

AGTTCCAGTG CCTGTTTGAC CCTGTTTAAC ACAAGATGGC CACCTGGACC ATCTTTATTT      600

ACATAATGTT TTACATCAGC ACTTCCTGTA TTCAGCCCTA AACTTAAAGA GGCCTCACTT      660

CCTGATGATC TGGTGACACC TGCTGGTTGA AGGAAACAGA GTTTGAGAGG CAGCAGAACA      720

AATGATTTTA GTTTGAATGA AGAAGCTGTC ATTTGATTTT ATGTTTGGAG GGGGGGGGGG      780

GGGGGATCAC CACACACAGA TATTGAACAC TGTCATCACT GAGTTCGGTG AAAGTGAAGA      840

ACCAGTACAT GTTGTGATAT ATAATATAAT CATAATAATT ATAATAATAC CATTAATCTC      900

TGCAGAATCA CTGACATCAA CATGGACGCA CCAGCCAAAG CCGCCGCAGC CACCGCCGCC      960

GCCGCCAAGG CCGCCGCAGA AGCCACCGCC GCCGCAGCTG CCAAAGCAGC AGCCGCCACC     1020

AAAGCCGGAG CAGCCCGTTA ATGATCGTGG TCGTCTTGAT GTGGGATCAT GTGAACATCT     1080

GAGCAGCGAG ATGTTACCAA TCTGCTGAAT AAACCTGAGA AGCTGATTGT TAAAAACCAA     1140

GTGTCCTGTT CATTTCATCT CTGAAAGTCC GTCACAGTTT CTGTAGATCA TGTAGACTCC     1200

AGGAAGTGAT GCCATTGTGC TGTTGAACCT GCAGGG                              1236
```

(2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

```
CATCAACATG GACGCACCAG CC                                                22
```

(2) INFORMATION FOR SEQ ID NO:35:

(i) SEQUENCE CHARACTERISTICS:
        (A) LENGTH: 39 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:35:

```
Met Asp Ala Pro Ala Lys Ala Ala Ala Ala Thr Ala Ala Ala Ala Lys
1               5                  10                  15

Ala Ala Ala Glu Ala Thr Ala Ala Ala Ala Lys Ala Ala Ala Ala
            20                  25                  30

Thr Lys Ala Ala Ala Ala Arg
        35
```

(2) INFORMATION FOR SEQ ID NO:36:

(i) SEQUENCE CHARACTERISTICS:
        (A) LENGTH: 39 amino acids
        (B) TYPE: amino acid (C) STRANDEDNESS:
          (D) TOPOLOGY: linear (ii) MOLECULE TYPE: protein (xi) SEQUENCE DESCRIPTION: SEQ ID NO:36:

Met Asp Ala Pro Ala Lys Ala Ala Ala Thr Ala Ala Ala Ala Lys
1               5                   10                  15

Ala Ala Ala Glu Asp Thr Ala Ala Lys Ala Lys Ala Ala Ala Asp
                20                  25                  30

Thr Lys Ala Lys Ala Ala Arg
        35

(2) INFORMATION FOR SEQ ID NO:37:

(i) SEQUENCE CHARACTERISTICS:
          (A) LENGTH: 39 amino acids
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO:37:

Met Asp Ala Pro Ala Lys Ala Ala Ala Asp Thr Ala Ala Lys Ala Lys
1               5                   10                  15

Ala Ala Ala Glu Asp Thr Ala Ala Lys Ala Lys Ala Ala Ala Asp
                20                  25                  30

Thr Lys Ala Lys Ala Ala Arg
        35

(2) INFORMATION FOR SEQ ID NO:38:

(i) SEQUENCE CHARACTERISTICS:
          (A) LENGTH: 39 amino acids
          (B) TYPE: amino acid
          (C) STRANDEDNESS:
          (D) TOPOLOGY: linear (ii) MOLECULE TYPE: protein (xi) SEQUENCE DESCRIPTION: SEQ ID NO:38:

Ala Ala Ala Ala Ala Lys Ala Ala Ala Asp Thr Ala Lys Ala Lys
1               5                   10                  15

Ala Ala Ala Glu Asp Thr Ala Ala Lys Ala Lys Ala Ala Ala Asp
                20                  25                  30

Thr Lys Ala Lys Ala Ala Arg
        35

(2) INFORMATION FOR SEQ ID NO:39:

(i) SEQUENCE CHARACTERISTICS:
          (A) LENGTH: 37 amino acids
          (B) TYPE: amino acid
          (C) STRANDEDNESS:
          (D) TOPOLOGY: linear (ii) MOLECULE TYPE: protein (ix) FEATURE:
          (A) NAME/KEY: -
          (B) LOCATION: 1..37
          (D) OTHER INFORMATION: /note= "HPLC-6"

(xi) SEQUENCE DESCRIPTION: SEQ ID NO:39:

Asp Thr Ala Ser Asp Ala Ala Ala Ala Ala Ala Leu Thr Ala Ala Asn

```
              1               5              10              15
Ala Lys Ala Ala Ala Glu Leu Thr Ala Ala Asn Ala Ala Ala Ala
             20              25              30
Ala Ala Thr Ala Arg
         35
```

(2) INFORMATION FOR SEQ ID NO:40:

(i) SEQUENCE CHARACTERISTICS:
        (A) LENGTH: 395 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..395
        (D) OTHER INFORMATION: /label= "pseudogene" F2

(ix) FEATURE:
        (A) NAME/KEY: CDS
        (B) LOCATION: 185..304
        (D) OTHER INFORMATION: /product= "sAFP2" /note=
            "skin-type antifreeze polypeptide 2 (sAFP2)"

(xi) SEQUENCE DESCRIPTION: SEQ ID NO:40:

```
TTACAAAACA AGTTCATACT GGCCTGGATG GTCGCCACAC CTTCCTGTTG ATGTGAACCA      60

GTCGGAGCCG ACGCCCTGCT GCGTCACAAA ATCAAAGTGA ATAAATAGAG GCTGCTCCCT     120

AAAAGTTTTC ATCAGGACTT CAAACACTTT TCACTGTCGA CCACTCAGAA TCACTGACAT     180

CAACATGGAC GCACCAGCCA AGCCGCCGC AGCCACCGCC GCCGCCGCCA AGGCCGCCGC      240

AGAAGCCACC GCCGCCGCAG CTGCCAAAGC AGCAGCCGCC ACCAAAGCCG AGCAGCCCG      300

TTAATGATCG TGGTCGTCTT GATGTGGGAT CATGTGAACA TCTGAGCAGC GAGATGTTAC     360

CAATCTGCTG AATAAACCTG AGAAGCTGAT TGTTA                                395
```

(2) INFORMATION FOR SEQ ID NO:41:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..322
        (D) OTHER INFORMATION: /note= "probe pkenc 17"

(ix) FEATURE:
        (A) NAME/KEY: CDS
        (B) LOCATION: 182..292
        (D) OTHER INFORMATION: /product= "HPLC-8"

(xi) SEQUENCE DESCRIPTION: SEQ ID NO:41:

```
ACCACATCTT CATTTTGTAG TGAACCAGTG CTCCCTACAA GTTCTCAAAA TGGCTCTCTC       60

ACTTTTCACT GTCGGACAAT TGATTTTCTT ATTTTGGACA ATGAGAATCA CTGAAGCCAG     120

CCCCGACCCC GCAGCCAAAG CCGCCCCAGC AGCAGCTGCC GCCCCTGCCG CAGCCGCCCC     180

A GAC ACC GCC TCT GAC GCC GCC GCT GCA GCC GCC CTT ACC GCC GCC         226
  Asp Thr Ala Ser Asp Ala Ala Ala Ala Ala Ala Leu Thr Ala Ala
   1               5                  10                  15
```

```
AAT GCC GCC GCC GCC GCC AAA CTC ACC GCC GAC AAC GCC GCC GCC GCC      274
Asn Ala Ala Ala Ala Ala Lys Leu Thr Ala Asp Asn Ala Ala Ala Ala
             20                  25                  30

GCA GCA GCC ACC GCC AGA GGTTAAGGAT CGTGGTCGTC TTGATGTGGG              322
Ala Ala Ala Thr Ala Arg
            35
```

(2) INFORMATION FOR SEQ ID NO:42:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO:42:

```
Asp Thr Ala Ser Asp Ala Ala Ala Ala Ala Leu Thr Ala Ala Asn
 1               5                  10                  15

Ala Ala Ala Ala Ala Lys Leu Thr Ala Asp Asn Ala Ala Ala Ala
             20                  25                  30

Ala Ala Thr Ala Arg
            35
```

(2) INFORMATION FOR SEQ ID NO:43:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Xaa Leu Thr Xaa Xaa Asn
 1               5
```

(2) INFORMATION FOR SEQ ID NO:44:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

```
Xaa Thr Xaa Xaa Asp Xaa
 1               5
```

(2) INFORMATION FOR SEQ ID NO:45:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:45:

```
Xaa Lys Thr Xaa Xaa Asp Xaa
 1               5
```

(2) INFORMATION FOR SEQ ID NO:46:

-continued

```
    (i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:46:

Xaa Asp Thr Xaa Xaa Lys Xaa
1               5
```